(12) United States Patent
Achiluzzi

(10) Patent No.: US 10,143,550 B2
(45) Date of Patent: Dec. 4, 2018

(54) HEART VALVE PROSTHESIS

(71) Applicant: Sorin Group Italia S.r.l., Mirandola (MO) (IT)

(72) Inventor: Monica F. Achiluzzi, Chivasso (IT)

(73) Assignee: Sorin Group Italia S.r.l., Milan (IT)

( * ) Notice: Subject to any disclaimer, the term of this patent is extended or adjusted under 35 U.S.C. 154(b) by 279 days.

(21) Appl. No.: 14/910,975

(22) PCT Filed: Jul. 17, 2014

(86) PCT No.: PCT/IB2014/063176
§ 371 (c)(1),
(2) Date: Feb. 8, 2016

(87) PCT Pub. No.: WO2015/019217
PCT Pub. Date: Feb. 12, 2015

(65) Prior Publication Data
US 2016/0193044 A1     Jul. 7, 2016

(30) Foreign Application Priority Data
Aug. 8, 2013 (EP) .................... 13425113

(51) Int. Cl.
*A61F 2/24* (2006.01)
(52) U.S. Cl.
CPC .......... *A61F 2/2418* (2013.01); *A61F 2/2409* (2013.01); *A61F 2/2436* (2013.01);
(Continued)
(58) Field of Classification Search
CPC .... A61F 2/2418; A61F 2/2409; A61F 2/2436; A61F 2220/0033; A61F 2230/0069
(Continued)

(56) References Cited

U.S. PATENT DOCUMENTS

| 5,855,601 | A  | 1/1999 | Bessler et al. |
| 6,287,339 | B1 | 9/2001 | Vazquez et al. |

(Continued)

FOREIGN PATENT DOCUMENTS

| CN | 102869319 A | 1/2013 |
| EP | 0133420 B1  | 2/1988 |

(Continued)

OTHER PUBLICATIONS

International Search Report and Written Opinion issued in PCT/IB2014061436, dated Oct. 20, 2014, 9 pages.

(Continued)

*Primary Examiner* — Vy Bui
(74) *Attorney, Agent, or Firm* — Faegre Baker Daniels LLP

(57) ABSTRACT

A heart valve prosthesis configured to be implanted at cardiac valve annulus located at an interface between a ventricle (LV) and an atrium (LA), the heart valve prosthesis including:
a first portion configured for enclosing a plurality of chordae tendineae (CT) in the ventricle (LV) and native valve leaflets (NVL) to which said chordae tendineae are connected, and
a second portion including a radially expandable annular member and a prosthetic heart valve anchored to said radially expandable annular member,
wherein said first portion is configured to be implanted in the ventricle (LV), and
wherein said second portion is configured to be implanted and coupled to the first portion at the cardiac valve annulus.

13 Claims, 17 Drawing Sheets

(52) U.S. Cl.
CPC ..... *A61F 2/2457* (2013.01); *A61F 2220/0033* (2013.01); *A61F 2230/0069* (2013.01); *A61F 2250/006* (2013.01)

(58) Field of Classification Search
USPC .............................................. 623/2.11, 2.14
See application file for complete search history.

(56) References Cited

U.S. PATENT DOCUMENTS

| | | |
|---|---|---|
| 6,312,465 B1 | 11/2001 | Griffin et al. |
| 6,425,916 B1 | 7/2002 | Garrison et al. |
| 6,458,153 B1 | 10/2002 | Bailey et al. |
| 6,461,366 B1 | 10/2002 | Seguin |
| 6,530,952 B2 | 3/2003 | Vesely |
| 6,569,196 B1 | 5/2003 | Vesely |
| 6,629,534 B1 | 10/2003 | St. Goar et al. |
| 6,821,297 B2 | 11/2004 | Snyders |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,018,408 B2 | 3/2006 | Bailey et al. |
| 7,252,682 B2 | 8/2007 | Seguin |
| 7,329,278 B2 | 2/2008 | Seguin et al. |
| 7,381,220 B2 | 6/2008 | Macoviak et al. |
| 7,556,646 B2 | 7/2009 | Yang et al. |
| 7,585,321 B2 | 9/2009 | Cribier |
| 7,648,528 B2 | 1/2010 | Styrc |
| 7,708,775 B2 | 5/2010 | Rowe et al. |
| 7,717,955 B2 | 5/2010 | Lane et al. |
| 7,753,949 B2 | 7/2010 | Lamphere et al. |
| 7,758,640 B2 | 7/2010 | Vesely |
| 7,776,083 B2 | 8/2010 | Vesely |
| 7,806,927 B2 | 10/2010 | Styrc |
| 7,892,281 B2 | 2/2011 | Seguin et al. |
| 7,959,672 B2 | 6/2011 | Salahieh et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,070,802 B2 | 12/2011 | Lamphere et al. |
| 8,105,375 B2 | 1/2012 | Navia et al. |
| 8,167,935 B2 | 5/2012 | McGuckin, Jr. et al. |
| 8,221,493 B2 | 7/2012 | Boyle et al. |
| 8,236,049 B2 | 8/2012 | Rowe et al. |
| 8,287,591 B2 | 10/2012 | Keidar et al. |
| 8,323,335 B2 | 12/2012 | Rowe et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,454,686 B2 | 6/2013 | Alkhatib |
| 8,540,767 B2 | 9/2013 | Zhang |
| 8,579,964 B2 | 11/2013 | Lane et al. |
| 8,579,966 B2 | 11/2013 | Seguin et al. |
| 8,597,348 B2 | 12/2013 | Rowe et al. |
| 9,186,249 B2 | 11/2015 | Rolando et al. |
| 2005/0137691 A1 | 6/2005 | Salahieh et al. |
| 2005/0182486 A1 | 8/2005 | Gabbay |
| 2006/0195183 A1 | 8/2006 | Navia et al. |
| 2007/0043435 A1 | 2/2007 | Seguin et al. |
| 2008/0140189 A1 | 6/2008 | Nguyen et al. |
| 2008/0208327 A1 | 8/2008 | Rowe |
| 2009/0125098 A1 | 5/2009 | Chuter |
| 2009/0248149 A1 | 10/2009 | Gabbay |
| 2009/0276040 A1 | 11/2009 | Rowe et al. |
| 2010/0004739 A1 | 1/2010 | Vesely |
| 2010/0145440 A1 | 6/2010 | Keranen |
| 2010/0174363 A1 | 7/2010 | Castro |
| 2010/0256741 A1 | 10/2010 | Hansen |
| 2010/0312333 A1 | 12/2010 | Navia et al. |
| 2011/0029072 A1 | 2/2011 | Gabbay |
| 2011/0071624 A1 | 3/2011 | Finch et al. |
| 2011/0098800 A1 | 4/2011 | Braido et al. |
| 2011/0137397 A1 | 6/2011 | Chau et al. |
| 2011/0166636 A1 | 7/2011 | Rowe |
| 2011/0178597 A9 | 7/2011 | Navia et al. |
| 2011/0218620 A1* | 9/2011 | Meiri ................. A61B 17/0487 623/2.11 |
| 2011/0224785 A1 | 9/2011 | Hacohen |
| 2011/0313515 A1 | 12/2011 | Quadri et al. |
| 2012/0010697 A1 | 1/2012 | Shin et al. |
| 2012/0016464 A1 | 1/2012 | Seguin |
| 2012/0022640 A1 | 1/2012 | Gross et al. |
| 2012/0046742 A1 | 2/2012 | Tuval et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0165930 A1* | 6/2012 | Gifford, III ........... A61F 2/2418 623/2.36 |
| 2012/0303116 A1 | 11/2012 | Gorman et al. |
| 2013/0018449 A1 | 1/2013 | Bailey et al. |
| 2013/0035759 A1 | 2/2013 | Gross et al. |
| 2013/0053950 A1 | 2/2013 | Rowe et al. |
| 2013/0144381 A1 | 6/2013 | Quadri et al. |
| 2013/0211508 A1 | 8/2013 | Lane et al. |
| 2013/0245753 A1 | 9/2013 | Alkhatib |
| 2013/0253643 A1 | 9/2013 | Rolando et al. |
| 2014/0046434 A1 | 2/2014 | Rolando et al. |

FOREIGN PATENT DOCUMENTS

| | | |
|---|---|---|
| EP | 0155245 B1 | 5/1990 |
| EP | 0515324 B1 | 11/1992 |
| EP | 1233731 B1 | 11/1999 |
| EP | 1049425 B1 | 11/2000 |
| EP | 1176913 B1 | 2/2002 |
| EP | 1251803 B1 | 10/2002 |
| EP | 1335683 B1 | 8/2003 |
| EP | 1343438 B1 | 9/2003 |
| EP | 1401359 B1 | 3/2004 |
| EP | 1408850 B1 | 4/2004 |
| EP | 1562502 A1 | 8/2005 |
| EP | 1562522 B1 | 8/2005 |
| EP | 1621162 B1 | 2/2006 |
| EP | 1701668 B1 | 9/2006 |
| EP | 1758523 B1 | 3/2007 |
| EP | 1935378 A1 | 6/2008 |
| EP | 1690515 B1 | 7/2008 |
| EP | 2000115 B1 | 12/2008 |
| EP | 2072027 A1 | 6/2009 |
| EP | 2078498 B1 | 7/2009 |
| EP | 2138132 B1 | 12/2009 |
| EP | 2250976 A1 | 11/2010 |
| EP | 2258312 B1 | 12/2010 |
| EP | 2260796 B1 | 12/2010 |
| EP | 2260797 B1 | 12/2010 |
| EP | 2260798 B1 | 12/2010 |
| EP | 2340075 B1 | 7/2011 |
| EP | 2641569 A1 | 3/2012 |
| EP | 2476394 B1 | 7/2012 |
| EP | 2486893 A1 | 8/2012 |
| EP | 2526895 B1 | 11/2012 |
| EP | 2526898 B1 | 11/2012 |
| EP | 2526899 B1 | 11/2012 |
| EP | 2529696 B1 | 12/2012 |
| EP | 2529697 B1 | 12/2012 |
| EP | 2529698 B1 | 12/2012 |
| EP | 2529699 B1 | 12/2012 |
| EP | 2537487 B1 | 12/2012 |
| EP | 2695586 A1 | 2/2014 |
| EP | 2886083 A1 | 6/2015 |
| WO | WO2008091515 A2 | 7/2008 |
| WO | WO2011044994 A1 | 4/2011 |
| WO | WO2012063228 A1 | 5/2012 |
| WO | WO2013037805 A1 | 3/2013 |
| WO | WO2013075215 A1 | 5/2013 |
| WO | WO2013082454 A1 | 6/2013 |
| WO | WO2013096541 A1 | 6/2013 |
| WO | 2013128436 A1 | 9/2013 |

OTHER PUBLICATIONS

International Preliminary Report on Patentability issued in PCT/IB2014/061436, dated Nov. 24, 2016, 7 pages.

(56) References Cited

OTHER PUBLICATIONS

International Preliminary Report on Patentability issued in PCT/IB2014/063176, dated Feb. 18, 2016, 9 pages.
European Search Report issued in EP Application No. 12425060, completed Jun. 27, 2012, 7 pages.
European Search Report issued in EP Application No. 12425139, completed Jan. 16, 2013, 7 pages.
European Search Report issued in EP Application No. 13425113, dated Feb. 7, 2014, 6 pages.
International Search Report issued in PCT/IB2013/052090, dated Jul. 21, 2013, 4 pages.
International Search Report issued in PCT/IB2014/063176, dated Oct. 9, 2014, 12 pages.

* cited by examiner

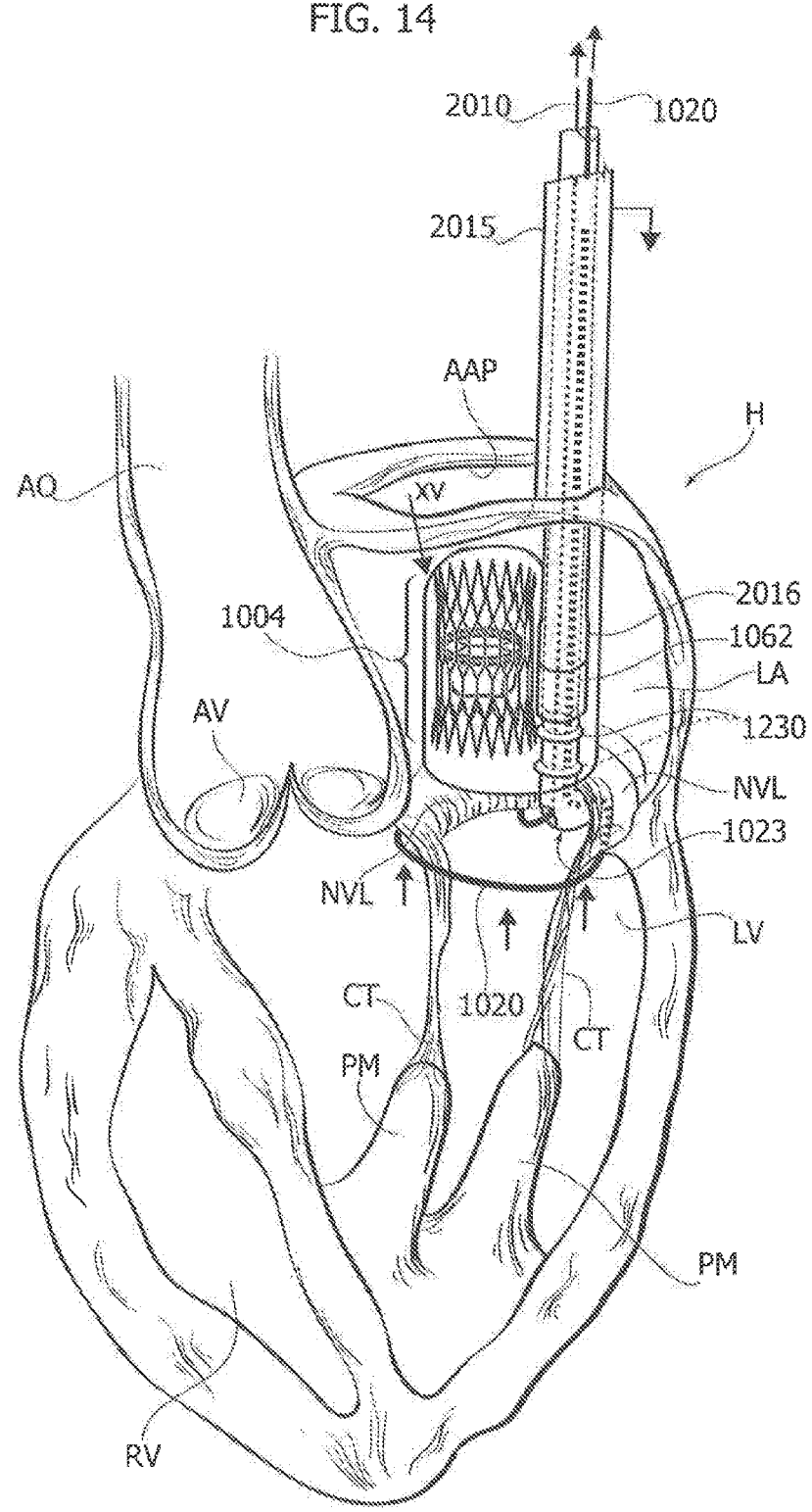

HEART VALVE PROSTHESIS

CROSS-REFERENCE TO RELATED APPLICATIONS

This application is a national phase application of PCT Application No. PCT/IB2014/063176, internationally filed Jul. 17, 2014, which claims priority to European Application No. 13 425 113.1, filed Aug. 8, 2013, all of which are herein incorporated by reference in their entirety.

TECHNICAL FIELD

The present description refers to heart valve prostheses and in particular to prostheses configured to be implanted in a patient's heart at an annulus which is located at an interface between a ventricle and an atrium of the heart, such as for example a mitral valve or a tricuspid valve.

BACKGROUND

Cardiac valve pathologies (for example stenosis or insufficiency) are generally treated surgically either with repair techniques or with replacement techniques. Repair techniques are believed to provide higher life expectancy and less morbidity after the surgical treatment than replacement techniques because, as a number of experts in the field have found, an important factor in determining the life expectancy and the morbidity lies in the conservation of native valve leaflets and chordae tendineae.

Valve repair techniques are characterized by the preservation and the restoration of the native valve leaflets and chordae tendineae, which are instead removed in valve replacement techniques in order to create the desired conditions for receiving the prosthesis at the implantation site.

However, the development of the cardiac valve prostheses in terms of structures, materials and fluid dynamics properties have come now to such a stage that even though a valve repair may provide a higher life expectancy due to the lower degree of alteration of the human body, a similar life expectancy is believed to be achievable also with such prostheses.

It is therefore an object of this disclosure that of providing a heart valve prosthesis which allows to dispense with the technical problems outlined above. In other words, it is an object of this disclosure that of providing a cardiac valve prosthesis presenting, altogether, the following properties:
ease of implantation,
simple design, and
improved life expectancy and lower morbidity after treatment for the patient.

SUMMARY

The objects in the foregoing are achieved by a cardiac valve prosthesis according to various embodiments as described in the following.

More particularly, according to various embodiments a heart valve prosthesis configured to be implanted at cardiac valve annulus located at an interface between a ventricle and an atrium, the heart valve prosthesis including:
a first portion configured for enclosing a plurality of chordae tendineae in the ventricle and native valve leaflets to which said chordae tendineae are connected, and
a second portion including a radially expandable annular member and a prosthetic heart valve anchored to said radially expandable annular member,
wherein said first portion is configured to be implanted in the ventricle, and
wherein said second portion is configured to be implanted and coupled to the first portion at the cardiac valve annulus.

BRIEF DESCRIPTION OF THE DRAWINGS

The invention will now be described with reference to the attached figures, provided purely by way of non limiting example, and wherein:

FIG. 14 is a view of a further step of the exemplary implantation sequence of the prosthesis according to FIG. 10, FIGS. 15 and 16 are partial sectional views of the ensemble indicated by the arrow XV in FIG. 14, again corresponding to yet different stages of the implantation sequence.

DETAILED DESCRIPTION

Figure 1:
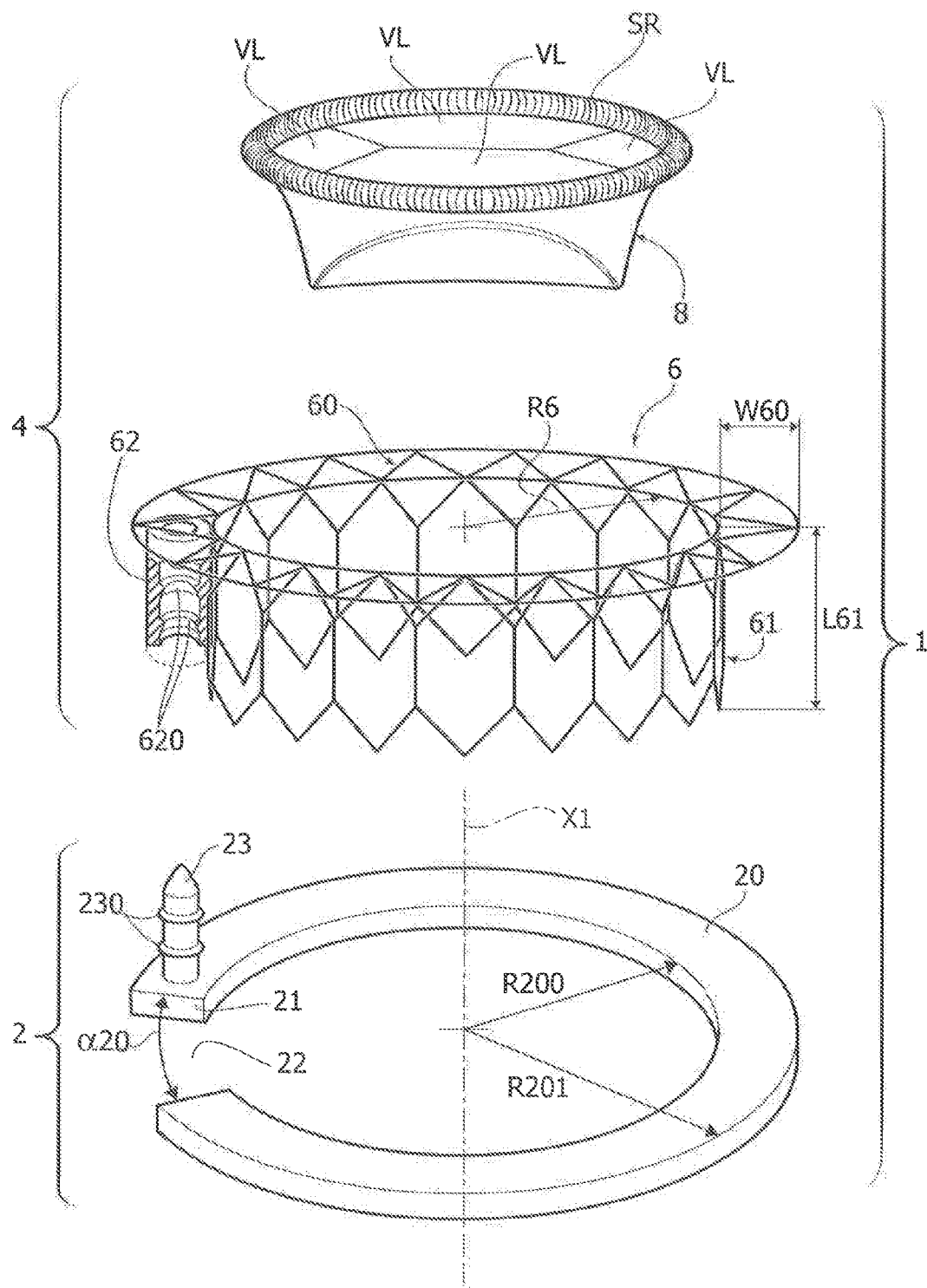
FIG. 1 is an exploded view of a heart valve prosthesis according to various embodiments.

In FIG. 1 the reference number 1 designates as a whole a heart valve prosthesis according to various embodiments. The heart valve prosthesis 1 includes a first portion 2 and a second portion 4 in turn including a radially expandable annular member 6 and a prosthetic heart valve 8 anchored to the radially expandable member.

In various embodiments, the first portion 2 takes the form of a spire-like element 20 having a general circumferential development and having a first and a second free ends 21, 22 facing each other.

Furthermore, in various embodiments the first portion 2 includes a plug member 23 (generally even more than one plug member, preferably two, maybe envisaged) provided on the spire-like element and orthogonal thereto (i.e. having an axis parallel to a main axis X1 of the spire-like element 20). In one embodiment, the plug member 23 is formed integrally with the spire-like element 20. In another embodiment, the spire-like element 23 is mechanically fastened to the spire-like element 20. In various embodiments, the plug member 23 is located near a free end of the spire-like element 20, in the embodiment depicted in FIG. 1 the free end 21.

The radially expandable member 6 includes in various embodiments a generally mesh-like or apertured structure (e.g. a stent-like structure) which allows significant radial deformations and therefore provides the radial expansion capability.

In various embodiments, the expandable annular member 6 may consist of a stent member including a first mesh portion integral with a second mesh portion 61. Both the mesh portions 60, 61 develop in a circumferential fashion but the first mesh portion 60 extends essentially in the radial direction (and possibly, in some embodiments, also in an axial direction so to have a general flared configuration) so to protrude radially with respect to the mesh portion 61, while the second mesh portion 61 is generally cylindrical in shape and therefore extends substantially in an axial direction.

In various embodiments, the mesh portion 60, 61 which make up the stent member 6 may be made of a shape memory material such as Nitinol. The stent member 6, in particular the mesh portion 60, furthermore includes a socket 62 which is configured to receive the plug member 23 and generally takes the shape of a cylindrical hollow member having one or more retention formations on the interior surface which are configured to cooperate with corresponding retention formations to provide a firm anchoring of the plug member 23.

In one embodiment, the plug member 23 may include circumferential ribs 230 which have a generally conical surface with a slope that converges towards the free end of the plug member 23.

Accordingly, the socket 62 may include complementary circumferential ribs 620 which have a generally conical surface with a slope oriented so to face the slope of the ribs 230 so to allow a movement of the plug 23 relative to the socket 62 only when the former is inserted into the latter and only in the direction of insertion, at least in part similar to the operation of a ratchet-and-pawl mechanism.

By way of generalization, the socket member in various embodiments may be configured to allow the movement of said plug member only in the direction of insertion so to avoid the separation of the second portion from the first portion once the prosthesis has been implanted. This may be achieved by a number of unidirectional coupling.

The socket 62 is permanently coupled to the stent member 6, and in some embodiments it may be mechanically connected thereto (for example by means of a small rivet). In other embodiments the socket 62 may even be made integral with the stent member 6 for example by means of soldering thereto.

With reference again to FIG. 1, the heart valve prosthesis is in various embodiments a prosthesis of the "biological" type. It is, in other words, a prosthesis which is sized and dimensioned and shaped in order to replicate both the structure and the behaviour of natural heart valves (i.e. provided with tissue-like coapting valve leaflets) and is made in a large majority of embodiments of biological tissue or even artificial material such as biocompatible polymers.

In various embodiments, the prosthetic heart valve 8 includes a sewing ring SR and a number of leaflets VL which is generally comprised between 2 and 4 leaflets. In FIG. 1 the prosthetic heart valve 8 includes, as an example, four leaflets VL, but the skilled man will appreciate that the number of leaflets will vary depending on the specific needs.

In various embodiments the prosthetic heart valve 8 is anchored to the expandable portion 6 for example by means of stitching. In other embodiments, specific adhesives may be used in alternative or in conjunction with the stitches. Furthermore, in some embodiments the prosthetic valve 8 may be anchored to the stent member 6 also by means of specifically designed, radially protruding fingers provided either on the mesh portion 60 or on the mesh portion 61 (or both) and configured to settle in the commissures of the prosthetic valve 8. Stitches may be passed through the commissures and the fingers so to firmly anchor the prosthetic valve 8 to the meshed structure 6.

With reference to FIGS. 2 to 5, an exemplary implantation sequence of the heart valve prostheses according to various embodiments herein described is shown.

Figure 2:
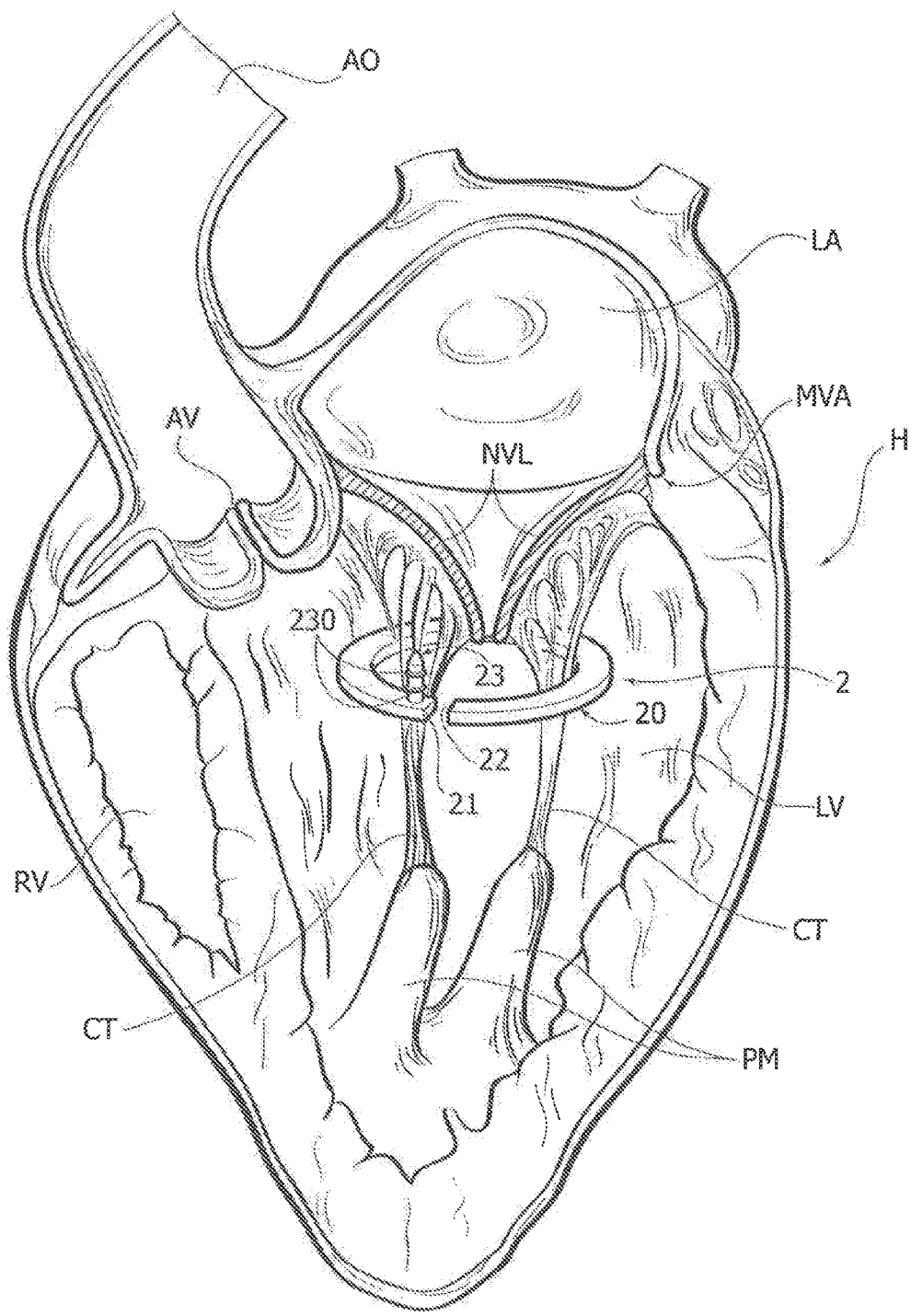
FIGS. 2 to 5 illustrate an exemplary implantation sequence of a heart valve prosthesis according to exemplary embodiments.

A first stage of the sequence is shown in FIG. 2, wherein a human heart H is represented in sectional view across the left ventricle and the left atrium. This means that in FIGS. 2 to 5, as a non-limiting example, a mitral valve replacement procedure is shown.

More specifically, in the sectional view of FIG. 2, the following elements of the human heart H are visible:
the aorta AO with the aortic valve AV,
the left ventricle LV and the papillary muscles PM located therein, as well as the native chordae tendineae CT which are connected to the native (mitral) valve leaflets NVL,
the mitral valve annulus MVA,
the left atrium LA, and
a portion of the right ventricle RV.

The implantation of the heart valve prosthesis 1 may be performed both with traditional surgical techniques or with the aid of the delivery catheters similar to those used in minimally invasive implantation procedures.

With reference to FIG. 2, in a first stage of the implantation procedure the practitioner may deliver the first portion 2 in the left ventricle LV with the spire-like element 20 collapsed to a smaller diameter with respect to its nominal (i.e. unconstrained) one. Thanks to the collapsed spire-like elements 20, the latter may be routed through the native valve leaflets NVL of the mitral valve then let to expand in the left ventricle.

The first portion 2 is configured to be implanted in the ventricle (it may be said that the portion 2 is a "ventricular" portion of the prosthesis 1) and it is configured to enclose a plurality of native chordae tendineae in the left ventricle and the native valve leaflets NVL to which said chordae tendineae are connected. The verb "to enclose" as used herein is intended to designate a situation in which the chordae tendineae and the native valve leaflets are contained within the portion 2, namely the spire-like member 20.

More to the point, when the spire-like element is its unconstrained condition, the practitioner may first let the chordae tendineae CT into the spire-like element 20 by leading them across the gap between the free ends 21, 22 (a further dilation of the spire-like element may also be envisaged if necessary). Then, the practitioner may encircle the chordae tendineae with the spire-like element 20 by using the plug member 23 as a sort of "pivot member" for controlling a rotation of the spire-like element 20 around the native chordae tendineae CT. The rotation may therefore be controlled around the axis of the plug element 23.

It is to be noted that the spire-like element 20 may be positioned both by means of a grasper or a similarly designed clamp or by means of a dedicated delivery system. Such a delivery system, not shown herein in detail, may comprise a hub whereon the spire-like element is retained in a collapsed configuration thanks to a slidable cap or sheath which is further configured to be displaced in order to allow the radial expansion of the spire-like element 20.

Advantageously a recall member may be provided, for example a guidewire, in order to have the possibility of displacing the spire-like element within the ventricle. If instead a grasper is used, the grasper itself may serve to displace the member 20.

Figure 3:
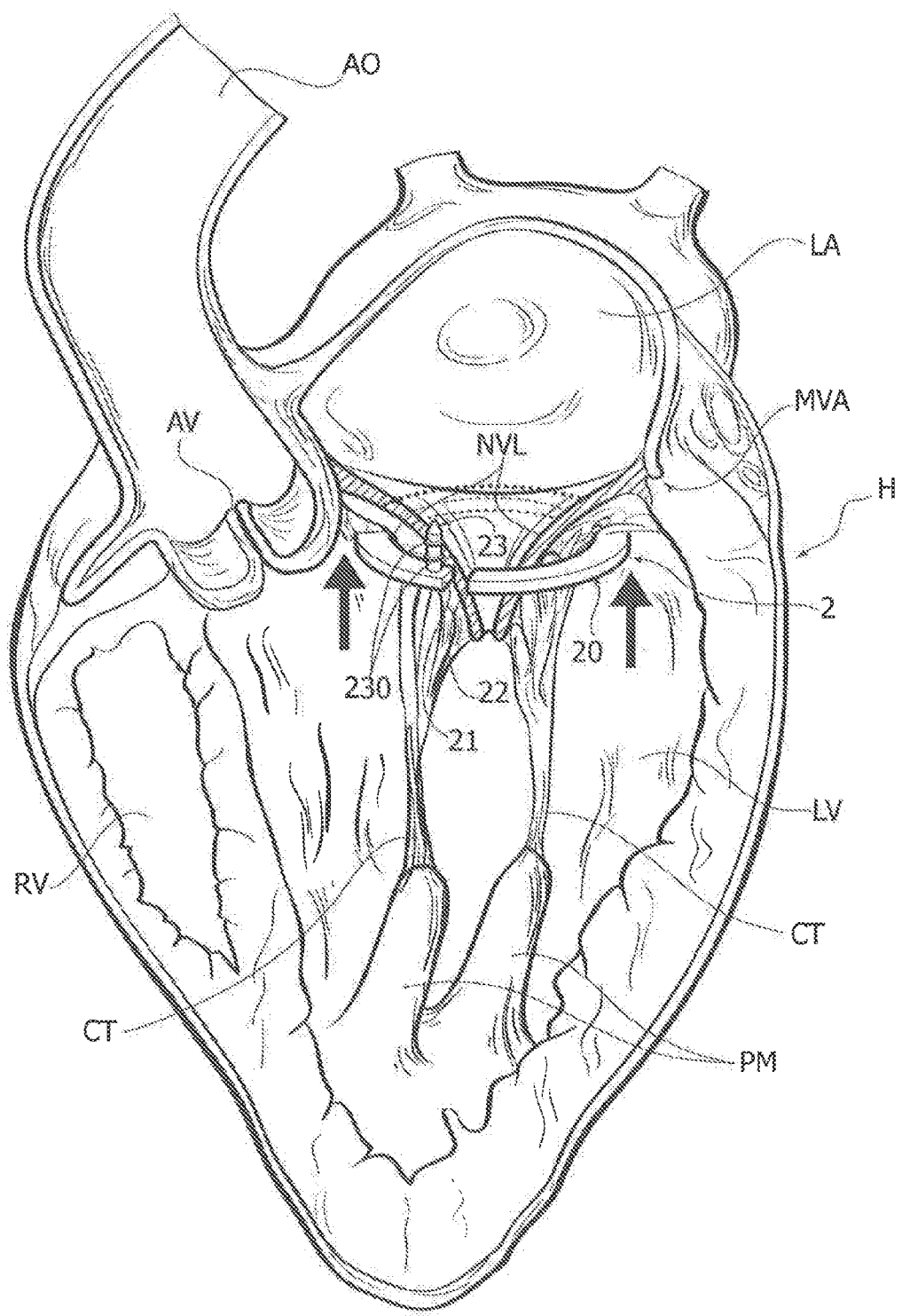

In various embodiments, after the first step shown in FIG. 2 the implantation procedure goes on with a step depicted in FIG. 3, wherein the spire-like element 20, already enclosing and encircling the native chordae tendineae CT, is displaced towards the native valve annulus NVA by means of either the recall member (e.g. a guidewire) or the grasper.

In this way, as shown in FIG. 3, both the chordae tendineae and the native mitral valve leaflets NVL are enclosed within the spire-like element 20, with the plug member 23 conveniently positioned with respect to the annulus so as to protrude through the commissures between the native valve leaflets NVL once the spire-like element has been brought in contact with the mitral valve annulus MVA.

It is furthermore to be noted that in various embodiments the plug member may be sized and dimensioned in order to have a blunt free end in order to avoid possible damages to the surrounding tissue.

In other embodiments, instead, the plug member 23 may be sized and dimensioned so to have a sharp free end (for example like a sting) thereby allowing for a piercing of the tissue of native valve leaflets.

In such embodiments, the design of the radially expandable portion 6 as well as the spire-like element 20 may be more feasible as the plug member 23 is not limited to be positioned between the commissures of the native valve leaflets but it may positioned at a location that ensures at the same time a firm anchoring of the spire-like element to the implantation site (for example a portion of the native valve annulus whereat the amount of the surrounding tissue is higher with respect to other locations) and a more effective positioning of the prosthetic valve 8 with respect to the expandable portion 6.

Figure 4:
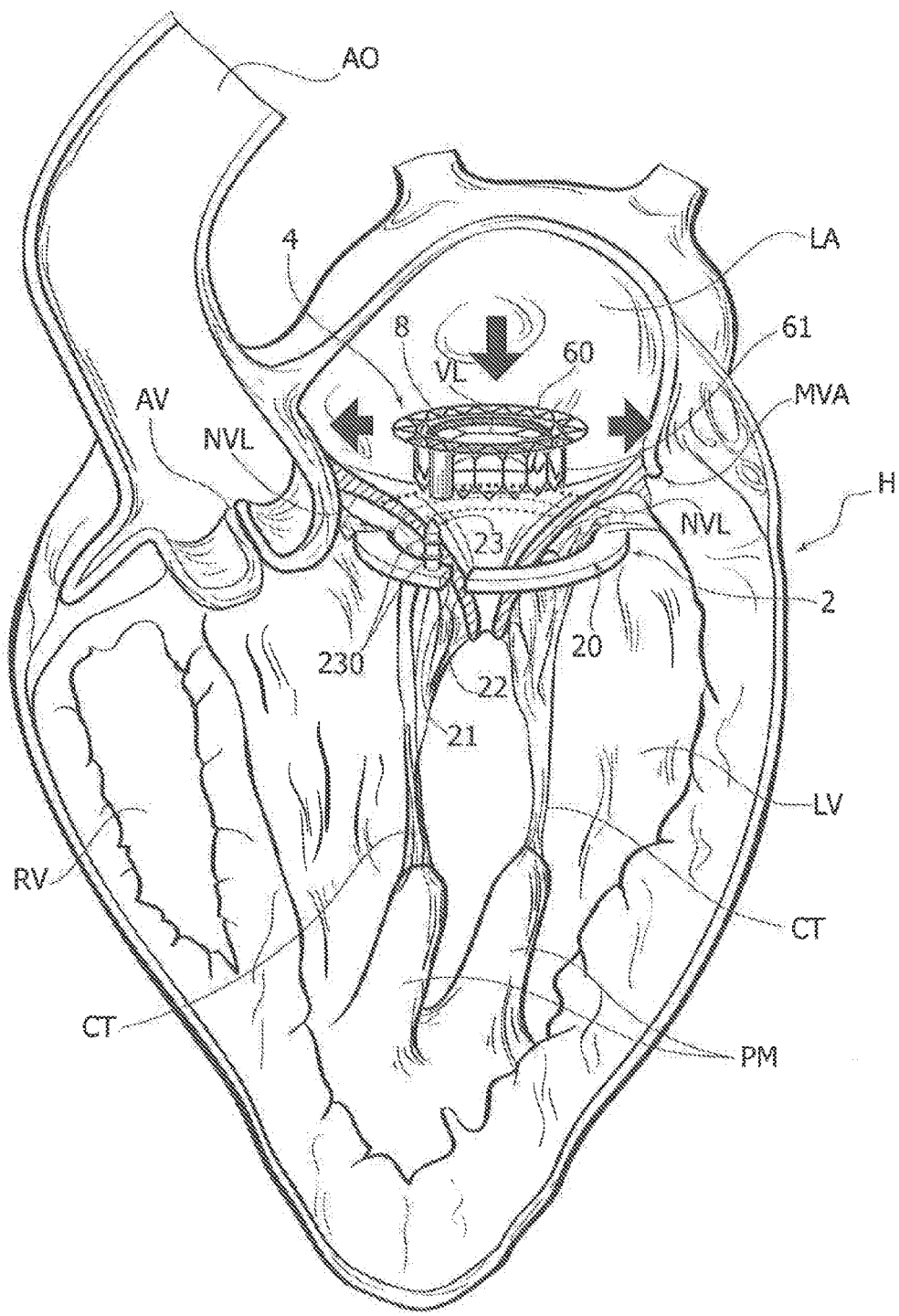

With reference to FIG. 4, once the spire-like element 20 has been located to its final position, the second portion is advanced towards the atrium of the heart H radially collapsed in a dedicated delivery system. Similarly to the delivery system which may be used with the spire-like element 20, the delivery system configured for use with the second portion 4, may be comprised of a hub which acts as a locking member for the collapsed stent member 6 and prosthetic valve 8 and a slidable sheet which retains the stent member 6 and the prosthetic valve 8 in the collapsed condition and that can be further displaced in an axial direction in order to release the collapsed portion 4 and let the stent member 6 to expand radially.

Whatever the structure of the delivery system, the whole second portion 4 is delivered at the mitral valve annulus (FIG. 4), as it is configured to be implanted and coupled to the first portion 2 at the native valve annulus itself.

Figure 5:
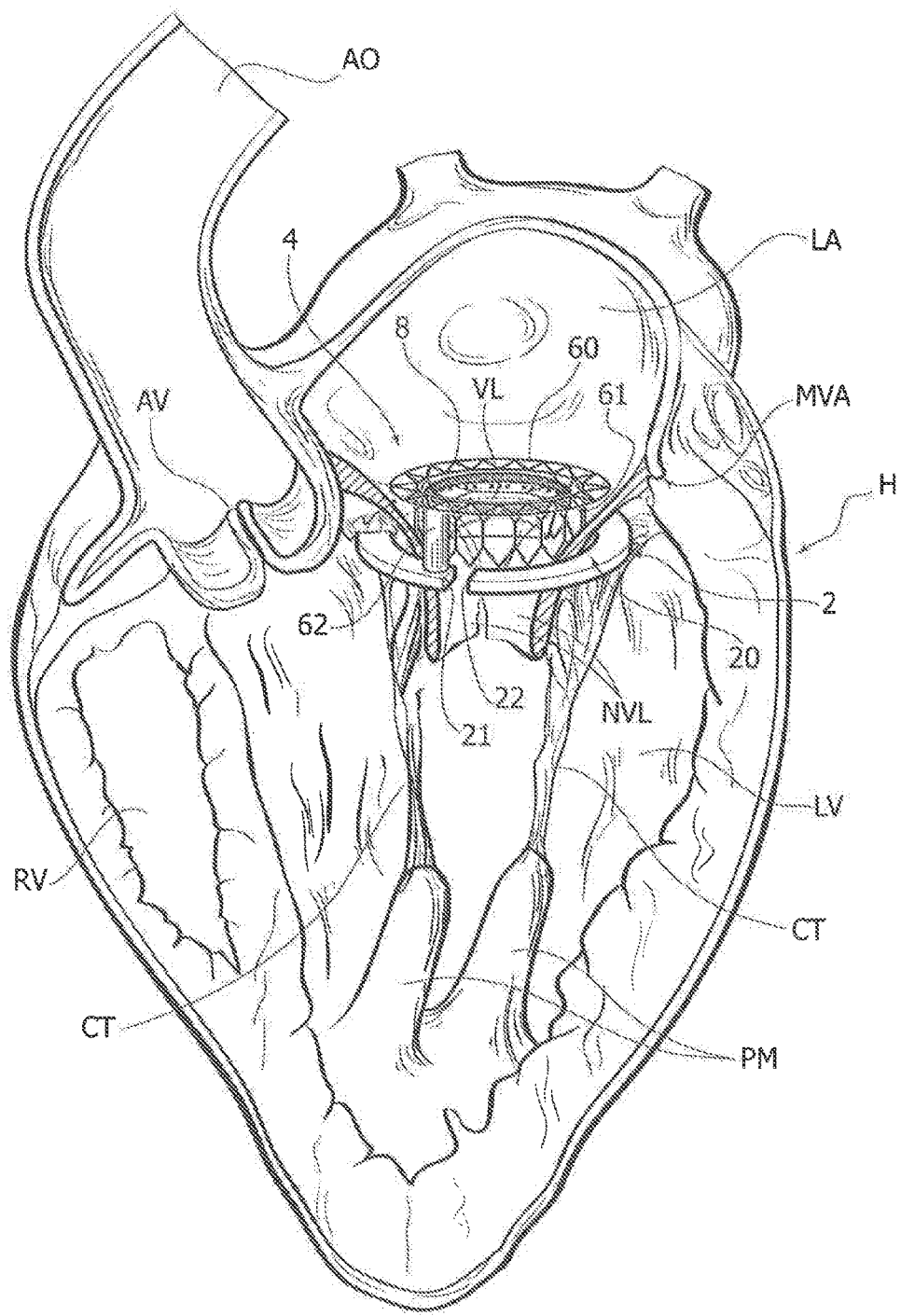

More specifically, the stent member 6 is made to expand at the native valve annulus so to trap the native valve leaflets (as well as the chordae tendineae) between itself and the spire-like element 20, as shown in FIG. 5. Upon expansion of the stent member 6, also a portion of the chordae tendineae CT which are enclosed within the spire-like element 20 are trapped between the latter and the stent member 6.

At the same time, the socket 62 is made to fit onto the plug member 23 which protrudes from the ventricle (either through the tissue surrounding the native valve annulus or through the commissures of the native valve leaflets, as described) so to firmly couple the second portion 4 to the first portion 2.

The final stage of the implantation procedure is shown in FIG. 5, wherein the whole second portion 4 is coupled to the first portion 2 which encircles and encloses a plurality of the native chordae tendineae CT in the left ventricle LV and the native valve leaflets NVL connected to the chordae tendineae CT.

Perivalvular leakage is reduced to a negligible amount thanks to the sealing action provided by the entrapment of the native valve leaflets between the sent member 6 and the spire-like element 20. Furthermore, unlike a traditional valve replacement procedure, the native chordae tendineae CT and the native valve leaflets NVL are maintained, so that a higher life expectancy and a lower morbidity with respect to traditional valve replacement procedures can be achieved.

As a further advantage it is to be noted that the heart valve prosthesis 1 according to various embodiments of the invention combines both of the advantages of a replacement intervention and a repair intervention, in that after the implantation of the prosthesis 1 the patient may take benefit from a, so to say, "brand new" and specifically engineered heart valve while also retaining the native chordae tendineae, the native valve leaflets the papillary muscle and whatever populates the interior of the left ventricle.

Figure 6:
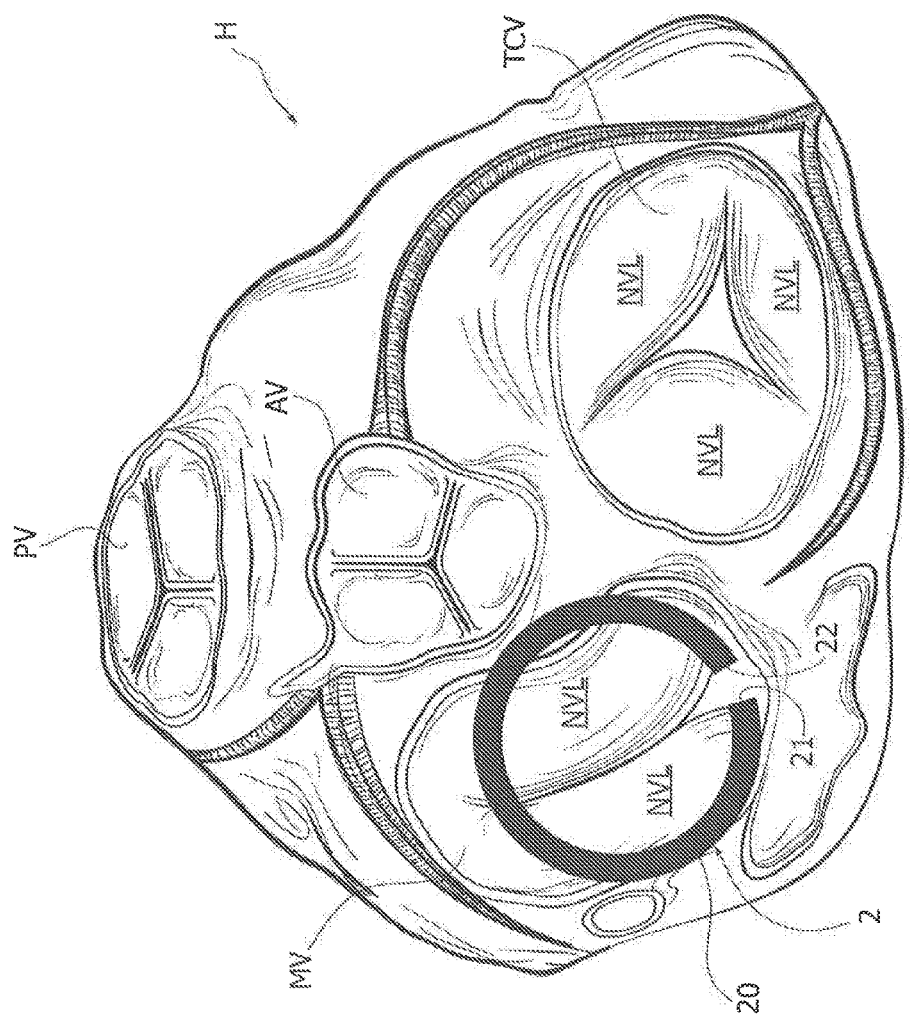
FIGS. 6 and 7 are top views of a human heart showing exemplary implantations of the heart valve prosthesis, and FIGS. 8 and 9 correspond to FIGS. 6-7 but show further exemplary implantations of the heart valve prosthesis.
Figure 7:
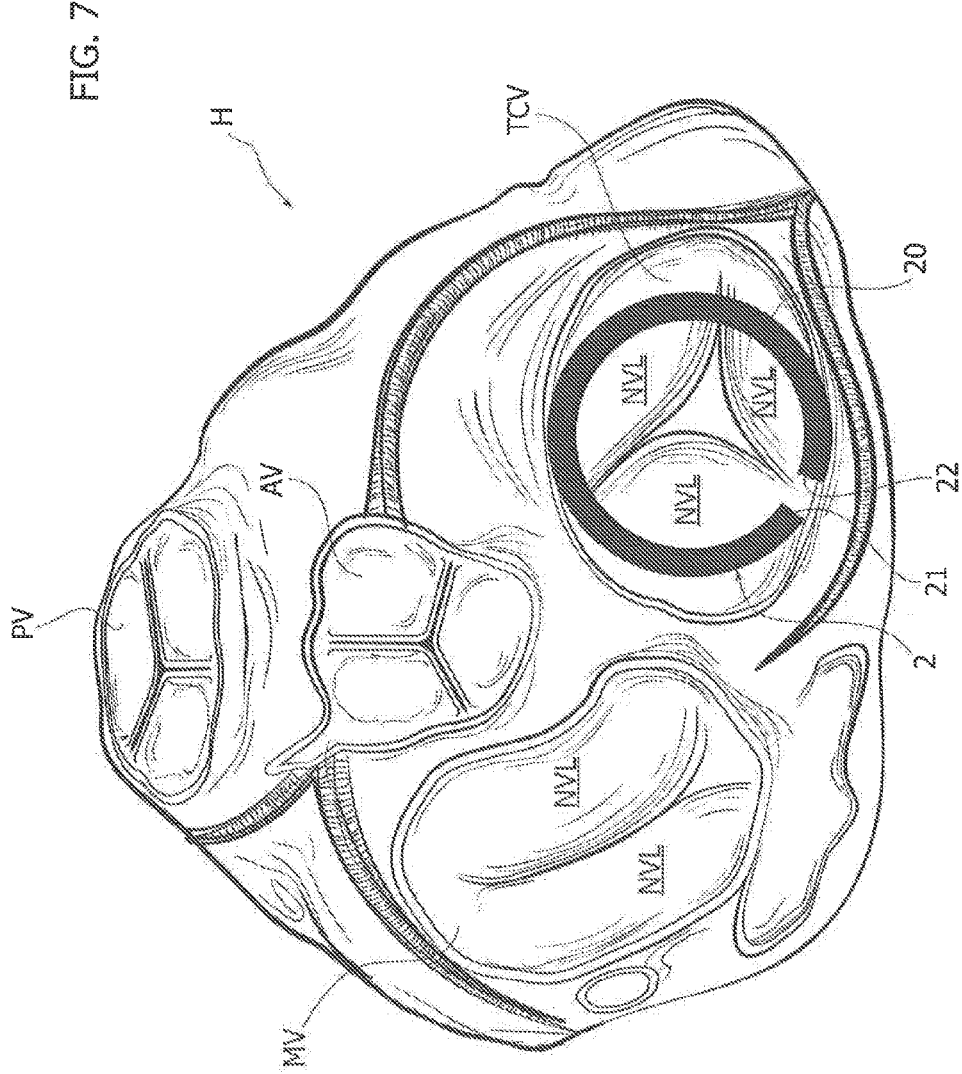

With reference to FIGS. 6 and 7, a top view of the human heart taken from the aorta shows the four cardiac valves in a substantially plan view. The four valves are labelled with the references MV for the mitral valve, TCV for the tricuspid valve, AV for the aortic valve and PV for the pulmonary valve.

As one can readily appreciate from FIGS. 6 and 7, the heart valve prosthesis according to various embodiments of the invention may be used wherever a native valve is located at an interface between a ventricle and an atrium of the human heart. This means in other words that the prosthesis 1 may be suitable both for replacing the mitral valve, as shown in FIG. 6, and for replacing the tricuspid valve as shown in FIG. 7.

FIGS. 6 and 7 both show the position of the spire-like element 20 relative to the native valve annulus in the case of the replacement of the mitral valve (FIG. 6) and tricuspid valve (FIG. 7). A spire-like element 20 is represented with a solid black line superimposed to the native heart valve in the top view of the human heart, but the skilled man will readily appreciate, in view of the foregoing disclosure, that the spire-like element 20 is positioned below the valve annulus and that the representation given in FIGS. 6 and 7 is purely schematic and it is intended to facilitate the understanding of the disclosure.

With the positioning depicted in FIGS. 6 and 7 the plug member 23 is located in corresponding of a commissure of the native valves (either mitral or tricuspid), as the gap between the free ends 20, 21 is located substantially in a region corresponding to the commissures themselves.

Figure 8:
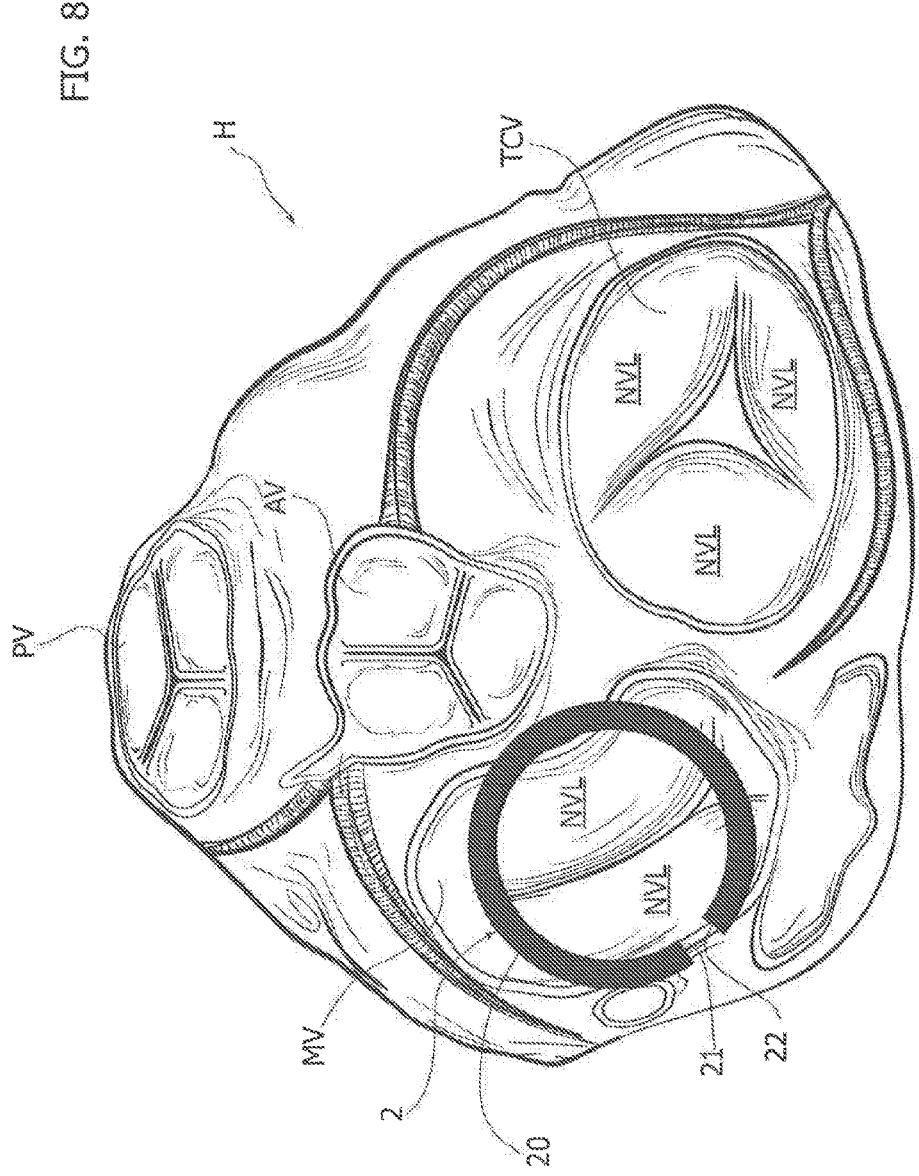
Figure 9:
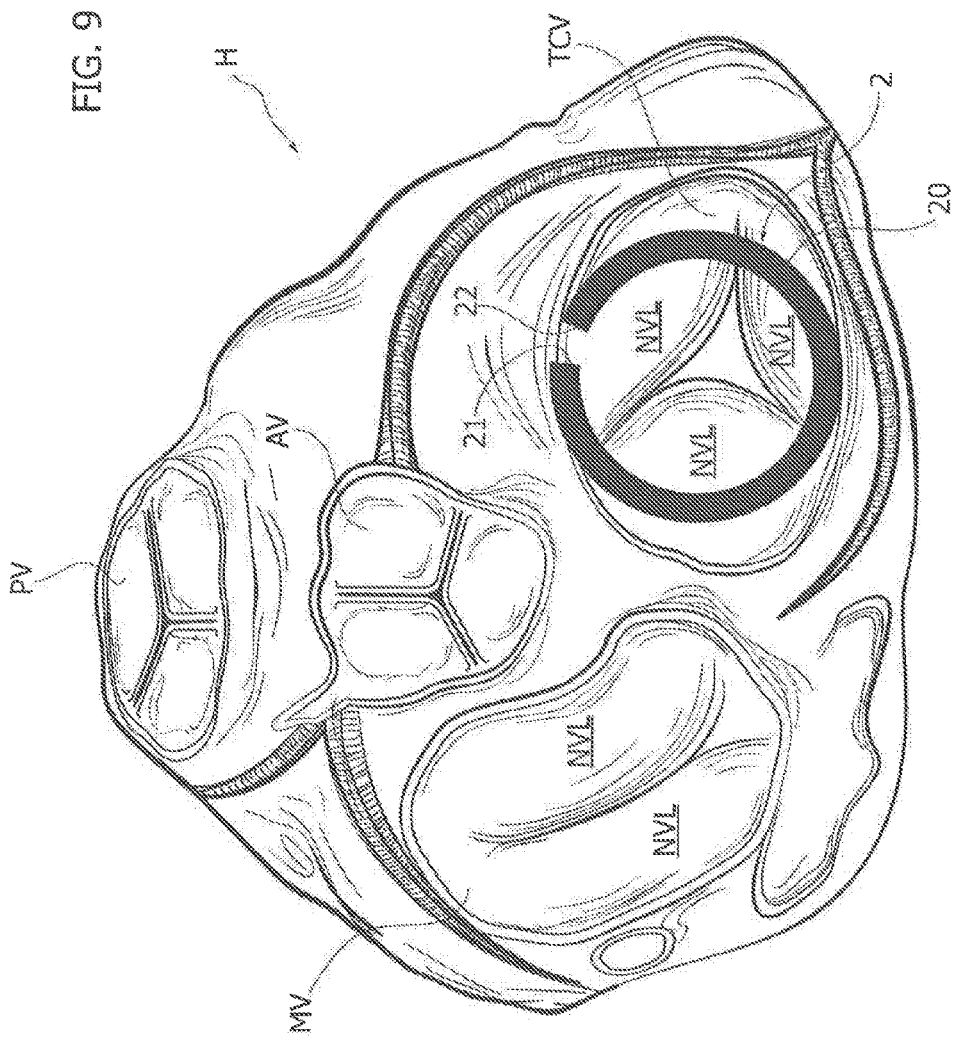

Other examples of radial positioning of the spire-like element 20 with respect to the native valve annulus are shown in FIGS. 8 and 9, which show examples of the heart valve prosthesis 1 wherein the plug member 23 is configured for piercing the tissue surrounding the native annulus and/or the native valve leaflets.

As already stated, the location at which the plug 23 pierces the native annulus and/or the native valve leaflets is chosen so to intercept a region wherein the amount of tissue is such as ensure on one side a firm anchoring of the prosthesis 1 to the implantation site and on the other side a minimum impact on the heart.

With reference again to FIG. 1, a number of representative dimensions of the prosthesis 1 has been assigned corresponding references, specifically:

R6 for the inner radius of the mesh portion 61,
W60 for the width of the mesh portion 60,
L61 for the axial length of the mesh portion 61,
R200 and R201 for the radiuses, respectively internal and external of the spire-like element 20, and
α20 for the angle between the free ends 21, 22 of the spire-like element 20.

In various embodiments, the radius R6 is chosen as a function of the geometry of the native valve annulus, also taking into account the presence of the native valve leaflets. It can therefore be assumed as a reference dimension according to which the other dimensions of the stent member 6 may be chosen.

For this reason, in one embodiment the ratio W60/R6 is chosen in the range between 0.1 and 0.2.

In some embodiments, the ratio L61/R6 is chosen in the range 0.7 to 1.

The radius R200 is generally chosen so as to encircle both the chordae tendineae CT and the native valve leaflets NVL and it is generally sized and dimensioned to be greater than the radius R6 in the expanded configuration of the stent member 6. Again, R200 can be assumed, similarly to R6, as a reference dimension according to which the remaining dimensions of the spire-like member 20 may be chosen. For this reasons, in one embodiment the ratio R201/R200 is chosen in the range 1.1 to 1.2.

The variation of the ratio R201/R200 may entail a corresponding variation in the circumferential flexibility of the spire like member 20: however, the choice thereof in the range indicated above essentially results in minor variations of the flexibility, which is instead preferably modulated by adding circumferential stiffening ribs or the like (preferably in embodiments wherein a sole plug member 23 is provided). The ratio R201/R200 is preferably kept within the above range essentially to privilege easy handling of the spire like member 20 when encircling the chordae tendineae: much higher values of the ratio R201/R200 may in fact result in an undesirable reduction of the available room for encircling the chordae tendineae.

The angle α20 is similarly chosen on the basis of the anatomy of the patient, primarily the chordae tendineae, again to privilege handling and comfort when encircling the latter. It is generally comprised in the range 30° to 40°.

Naturally, without departing from the principles of the inventions, the details and the embodiments may vary, even significantly, with respect to what has been described and illustrated, without departing from the scope of the invention as defined by the annexed claims.

For example, in various embodiments the entire stent member 6 may be covered with a biocompatible fabric or sheath (for example coated with biocompatible carbon) which enhances both the biocompatibility of the prostheses and the minimization of the perivalvular leakage.

Furthermore, in some embodiments the spire-like element 20 may be made of metal material, as well as the plug 23, while in other embodiments a polymeric material may be chosen. In both cases a biocompatible coating (e.g. pyrolitic carbon) may be applied on the surface of the spire-like element 20 in order to enhance the compatibility with the blood.

Concerning the plug member 23, in addition to the locking mechanism (similar to a ratchet-and-pawl mechanism) described above, in further embodiments the same snap fit action that characterizes the plug member 23 with the circumferential ribs 20 and the socket 62 with the circumferential ribs 620 may be achieved otherwise, for example by shaping the plug member 23 as a dowel. In some embodiments, furthermore, at least one further plug member (as well as a corresponding socket member) may be provided in the first portion 2 (as well as second portion 4 for the socket) in order to further enhance and improve the coupling between the first and second portions 2, 4. In some embodiments further plug members may be located in a position substantially diametrically opposite that of the first plug member, and in certain embodiments yet a further plug may be located in correspondence of the posterior leaflet of the mitral valve.

Figure 10:
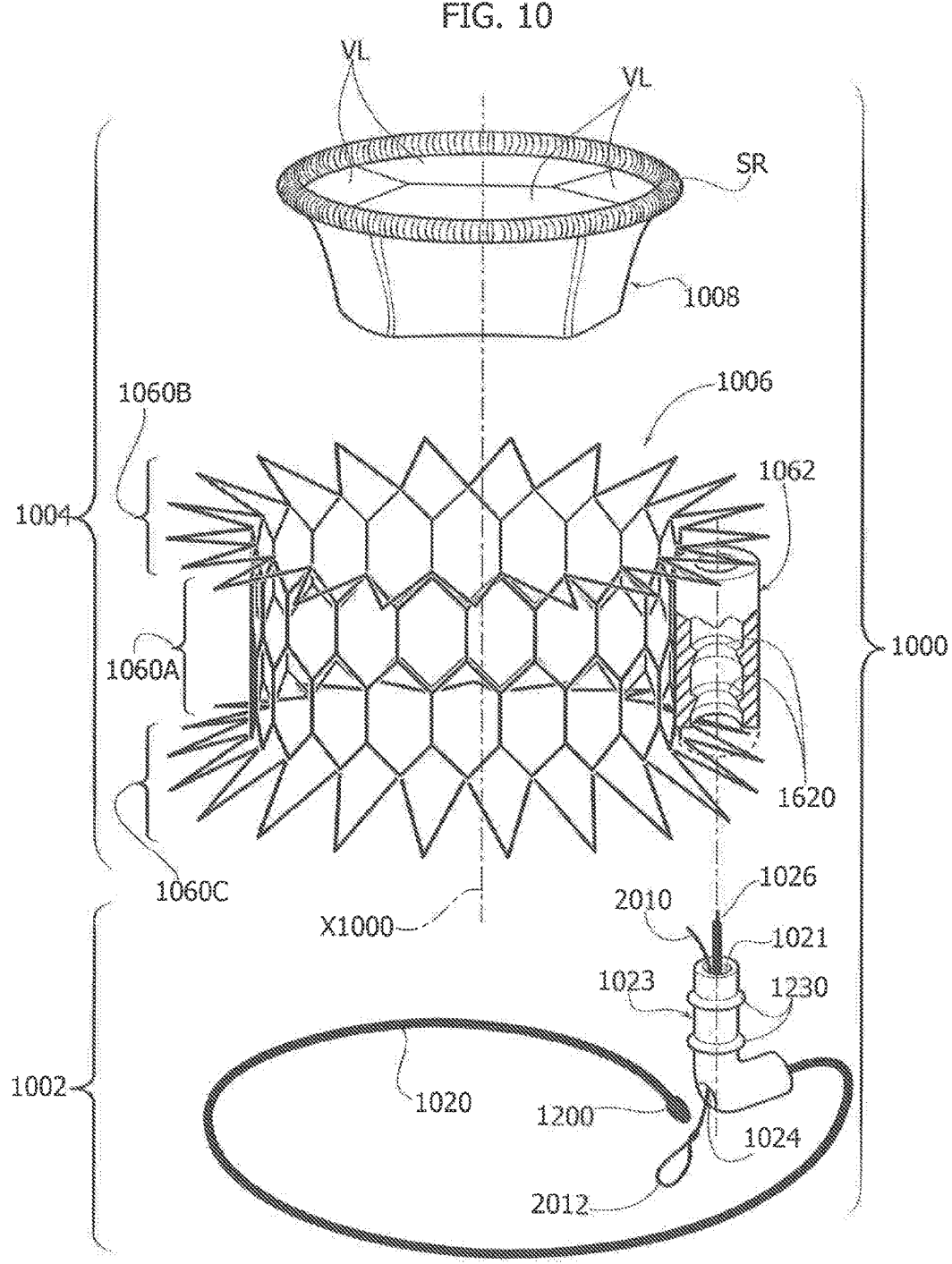
FIG. 10 is a perspective view of a heart valve prosthesis according to various further embodiments.

With reference to FIG. 10, the reference number 1000 designates as a whole a heart valve prosthesis according to further various embodiments. The heart valve prosthesis 1000 includes a first portion 1002 and a second portion 1004 in turn including a radially expandable annular member 1006 and a prosthetic heart valve 1008 anchored to the radially expandable annular member.

In various embodiments, as will be further detailed in the following, the first portion 1002 includes a deployable spire-like element 1020, herein shown deployed and protruding from a proximal portion of a deployment instrument sized and dimensioned so as to define a plug member 1023. The spire like element 1020 may be embodied as a thermoformed wire which is capable of recovering a substantially annular pattern from any shape that may be imparted thereto.

In various embodiments the plug member 1023 is embodied as an L-shaped tubular member having circular cross section and including, at one end thereof, a threaded portion 1021 (preferably with internal thread). On a stretch of the plug member 1023 adjacent the threaded portion 1021 one or more circumferential ribs 1230 are provided. Additionally, a through hole 1024 is provided essentially in correspondence of a knee of the plug member 1023.

The plug member 1023 is part of a deployment instrument depicted in FIG. 10A and designated as a whole by the reference 2000.

Figure 11:
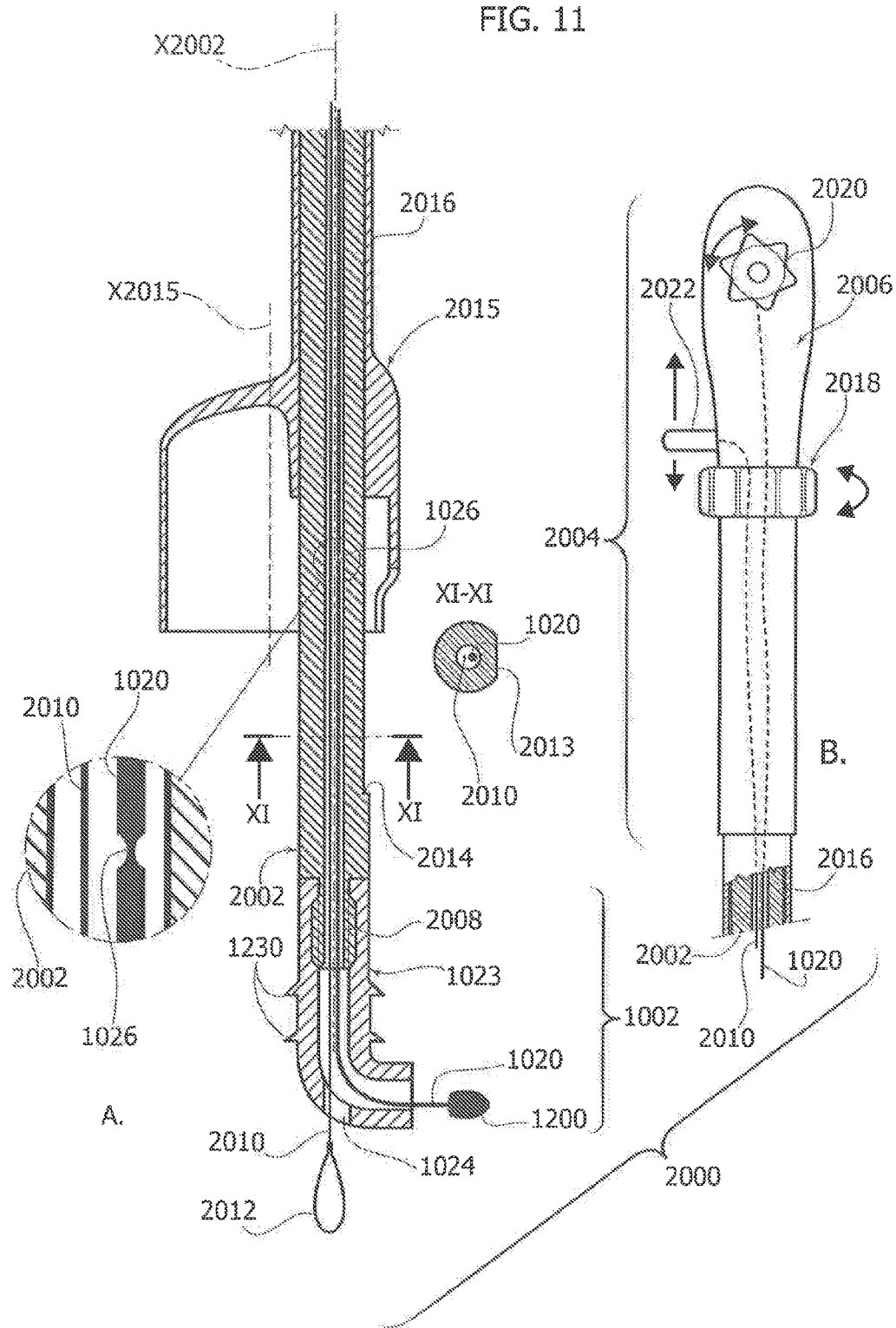
FIG. 11 is a sectional view, split in a first portion A and a second portion B, of an exemplary embodiment of an instrument for implanting the heart valve prosthesis according to FIG. 10.

The deployment instrument 2000 includes a proximal portion depicted in FIG. 11A and a distal portion depicted in FIG. 11B. The terms "proximal" and "distal as used herein refer to the implantation site.

In various embodiments, the proximal portion includes the plug member 1023, which defines a proximal tip of the deployment instrument 2000, and a shaft 2002 connected to the plug member 1023.

The distal portion (FIG. 11B), on the other hand, includes a manipulation assembly 2004 including a grip 2006 and one or more actuator members.

Turning now to the proximal portion, the shaft 2002 is releasably connected to the plug member 1023. Such releasable connection is in some embodiments—such as those depicted in FIG. 11—attained by means of a threaded end portion 2008, preferably having an external thread, which is configured to mate with the (internally) threaded portion 1021 of the plug member 1023.

The shaft 2002 in various embodiments takes the form of a tubular member (having therefore a hollow section) which houses the spire-like member 1020 in an extended (i.e. linear) configuration together with a wire-like member 2010. In various embodiments, the spire-like member 1020 is provided with an ogive-like member 1200 at a free end thereof, while the wire-like member 2010 terminates with a loop 2012. As visible from FIG. 11A, in an undeployed state, i.e. when both the spire-like member 1020 and the wire-like member 2010 are retracted inside the shaft 2002 and the plug member 1023, the ogive-like member 1200 may protrude outside of an end of the plug member 1023 opposite that where the threaded portion 1021 is located, whilst the wire-like member is arranged so that the loop 2012 comes out of the opening 1024. In various embodiments the spire like member 1020 is further provided with a weakened section 1026, better visible in the enlarged view of FIG. 11A (see the circle on the left). The weakened section 1026 has in one embodiment a reduced cross section, while in another embodiment it may include indentations, notches or other kind of carving in order to locally amplify the tensile stress.

In various embodiments, a major portion of the length of the shaft 2002 has furthermore a substantially D-shaped cross section, thereby exhibiting a flattened side surface 2013. Only a minor share of the length of the shaft 2002, located in the vicinity of the threaded portion 2008 exhibits a full circular cross section, defining thereby an abutment shoulder 2014 at which the flattened side surface (2013) terminates.

In such embodiments, a sheath 2015 is slidably mounted on the shaft 2002 and particularly on the flattened side surface 2013. The sheath 2015 is mounted off-center with respect to the shaft 2002, i.e. a central axis thereof (which may not be a symmetry axis, as in the embodiment depicted in FIG. 11), is offset (and parallel) with respect to a longitudinal axis X2002 of the shaft 2002. In various embodiments the slidable coupling between the sheath 2015 and the shaft 2002 may be achieved by means of a hub 2016, preferably an integral portion of the sheath 2015, which exhibits a D-shaped cavity matching the shape of the portion of the shaft 2002 whereon the flattened side surface 2013 is provided. It is moreover to be noted that the abutment shoulder 2014 defines in such embodiments essentially an axial stop element, as the hub 2016, once come into contact with the abutment shoulder 2014, would prevent the sheath 2015 from a further axial movement toward the proximal end of the instrument 2000 due to the change in shape (and the increase) of the cross section of the shaft 2002.

With reference now to FIG. 11B, in various embodiments the distal portion of the instrument 2000 includes a number of actuators, in this specific embodiment in the number of three, each coupled to a specific element of the instrument 2000.

With reference to FIG. 11B, in one embodiment the manipulation assembly 2004 includes a first actuator 2018 operatively connected to the sheath 2015, a second actuator 2020 operatively connected to the spire like member 1020 and a third actuator 2022 operatively connected to the wire-like member 2010.

According to the specific needs of the practitioner, each actuator may be embodied as either a linear-motion or a rotary-motion actuator. The former choice may be more suitable for fast-acting mechanisms (i.e. with higher transmission ratios), while the latter may be more suitable for slow-acting mechanisms (i.e. with lower transmission ratios). In the specific embodiment represented in FIG. 11, the actuators 2018 and 2020 are of the rotary-motion type, while the actuator 2022 is of the linear motion type, as also indicated by the corresponding solid arrows.

In other embodiments other combinations are possible.

Turning again to FIG. 10, in various embodiments the radially expandable member 1006 includes a generally mesh-like or apertured structure (e.g. a stent-like structure) which allows significant radial deformations and therefore provides the radial expansion capability.

In such embodiments, the expandable annular member 1006 consists therefore of a stent member including a first mesh portion 1060A, of a generally cylindrical shape, integral with a second and third mesh portions 1060B, 1060C located at opposite ends thereof, both having a flared pattern when radially unconstrained.

Each of the mesh portions 1060A, 1060B, 1060C develops in a circumferential fashion but when deployed the second and third mesh portions 1060B, 1060C extend essentially in the radial direction (and to a minor extent also in the axial direction due to the generally flared configuration) so to protrude radially with respect to the first mesh portion 1060A, which instead is generally cylindrical in shape and therefore extends substantially in an axial direction.

In various embodiments, the mesh portions 1060A, 1060B, 1060C may be made of a shape memory material such as Nitinol.

In various embodiments a socket 1062 which is configured to receive the plug member 1023 is fixed to the stent member 1006, particularly to the mesh portion 1060A. The socket 1062 may generally take the shape of a cylindrical hollow member having one or more retention formations on the interior surface which are configured to cooperate with corresponding retention formations on the plug member 1023 to provide a firm anchoring to the plug member itself.

In one embodiment, the plug member 1023 may include—as retention formations—circumferential ribs 1230 which have a generally conical surface with a slope that converges towards the free end of the plug member 1023 (i.e. the threaded portion 1021).

Accordingly, the socket 1062 may include complementary circumferential ribs 1620 which have a generally conical surface with a slope oriented so to face the slope of the ribs 1230, thereby allowing a movement of the plug member 1023 relative to the socket 1062 only when the former is inserted into the latter and only in the direction of insertion, at least in part similar to the operation of a ratchet-and-pawl mechanism.

By way of generalization, the socket member in various embodiments may be configured to allow the movement of said plug member only in the direction of insertion so to avoid the separation of the second portion from the first portion once the prosthesis has been implanted. This may be achieved by a number of unidirectional couplings.

The socket 1062 is permanently coupled to mesh portion 1060A, for example by soldering thereto.

The heart valve prosthesis 1008 is in various embodiments completely identical to the heart valve prosthesis 8, therefore the description already provided in respect thereof still applies.

In particular, in various embodiments the prosthetic heart valve 1008 includes a sewing ring SR and a number of leaflets VL which is generally comprised between two and four leaflets. In FIG. 10 the prosthetic heart valve 1008 includes, as an example, four leaflets VL, but the skilled man will appreciate that the number of leaflets will vary depending on the specific needs.

In various embodiments the prosthetic heart valve 1008 is anchored to the expandable member 1006 for example by means of stitching. In other embodiments, specific adhesives may be used in alternative or in conjunction with the stitches. Furthermore, in some embodiments the prosthetic valve 1008 may be anchored to the stent member 1006 also by means of specifically designed, radially protruding fingers provided either on the mesh portion 1060A or on the mesh portion 1060B (or both) and configured to settle in the commissures of the prosthetic valve 1008.

Stitches may be passed through the commissures and the fingers so to firmly anchor the prosthetic valve 1008 to the mesh structure.

With reference to FIGS. 12 to 16, an exemplary implantation sequence of the heart valve prosthesis 1000 will be detailed in the following. By way of example, a mitral valve replacement has been chosen, but the same may be applied to the tricuspid valve.

Figure 12:
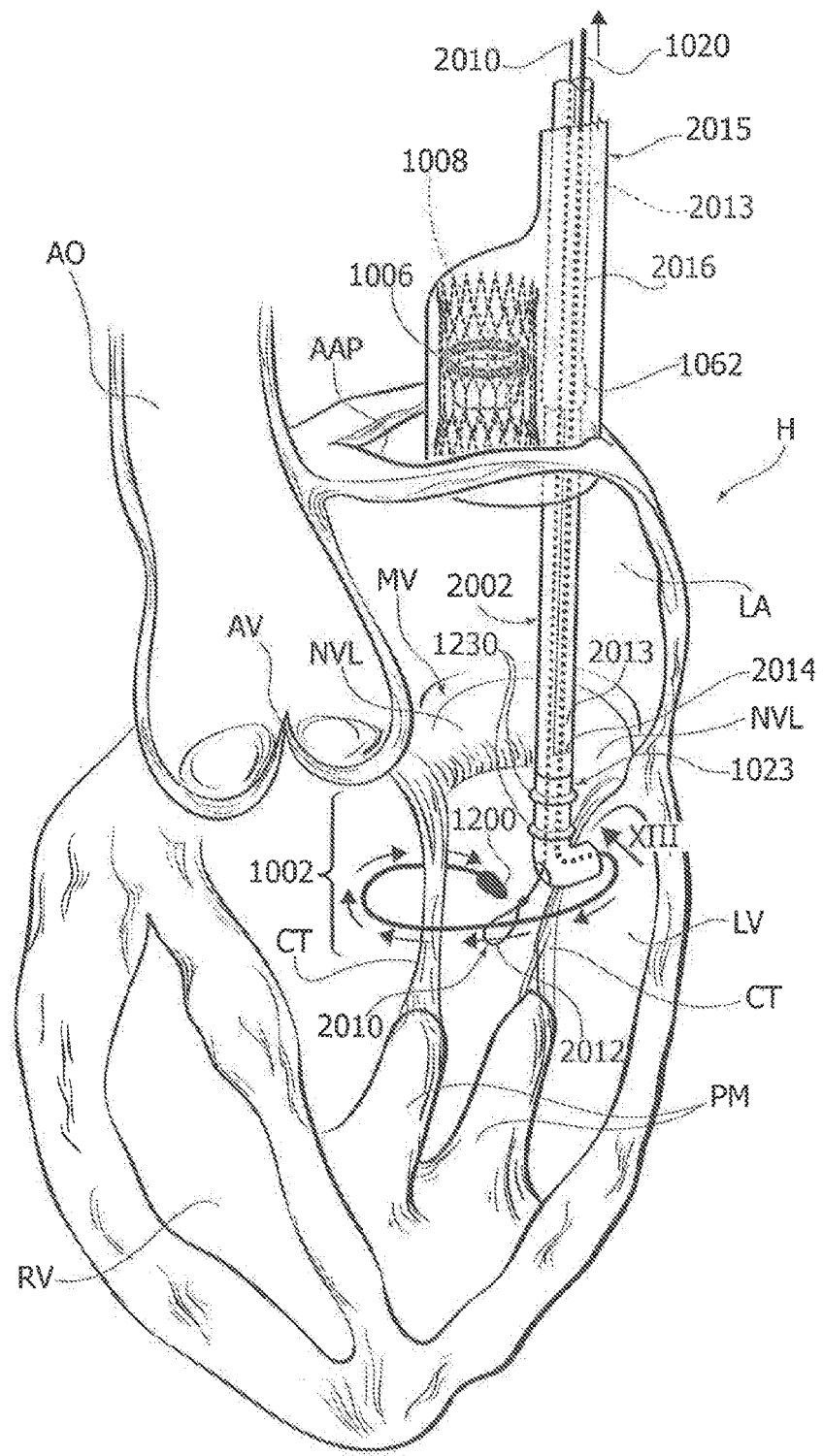
FIG. 12 is a view of a step of an exemplary implantation sequence of the prosthesis according to FIG. 10, FIGS. 13A and 13B are partial sectional views of the ensemble indicated by the arrow XIII in FIG. 12 corresponding to different stages of the implantation sequence.
Figure 15:
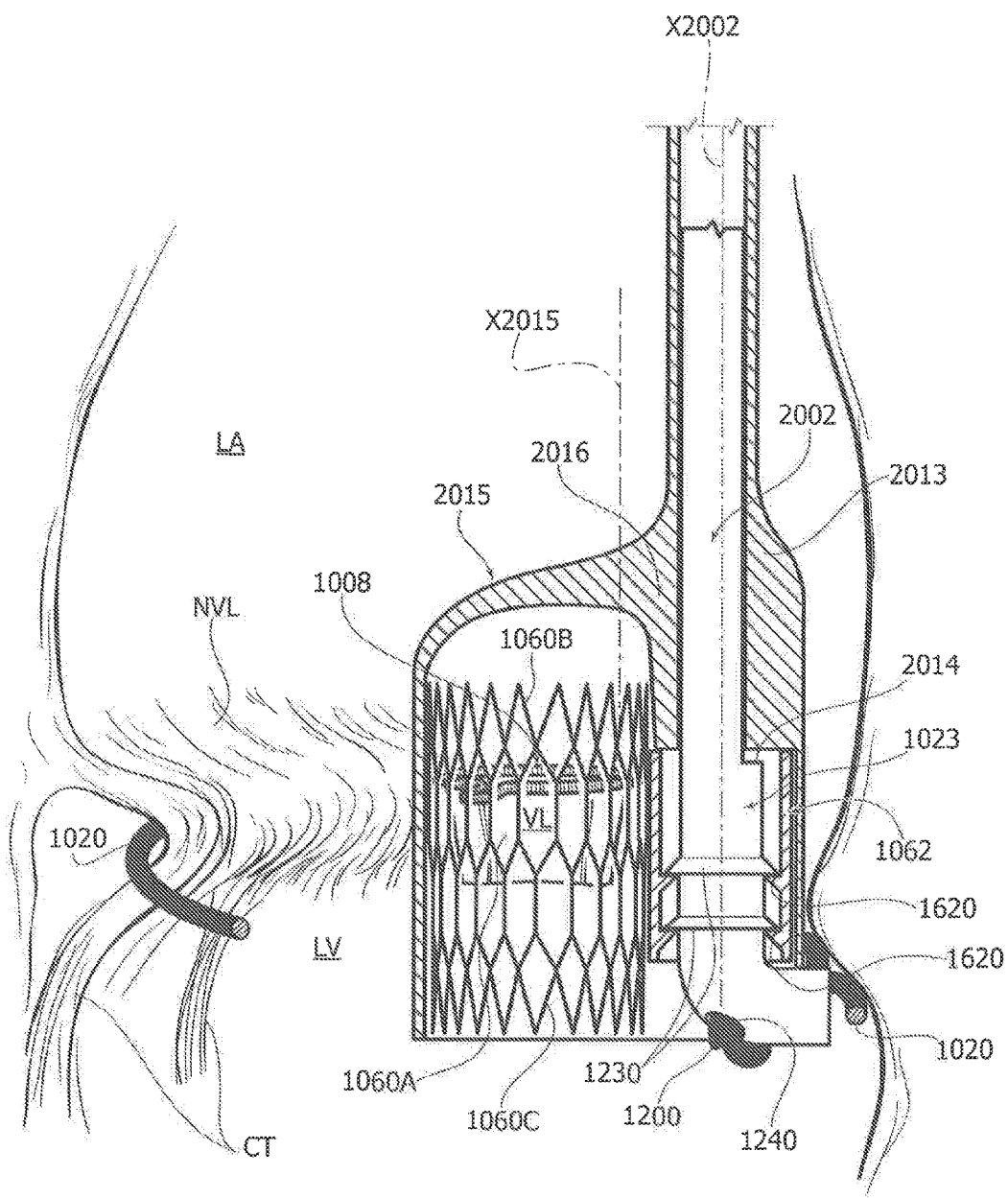

Reference is made now to FIGS. 12 and 15, the latter only to show a more detailed view of the coupling between the heart valve prosthesis 1000 and the instrument 2000.

In various embodiments, second portion 1004 is mounted on the instrument 2000 as shown in FIG. 15: the expandable annular member (stent member) 1006 with the prosthetic heart valve 1008 firmly anchored thereto is held radially collapsed into the sheath 2015 which unlike the view of FIG. 15 (which shows an advanced stage of the implantation sequence), is held at a distance from the abutment shoulder 2014.

The socket member 1062 is slidably mounted onto the shaft 2002 so that also the ensemble of the expandable member 1006 and the valve 1008 is located off-center with respect to the longitudinal axis X2002. Additionally, in various embodiments the hub 2016 is sized and dimensioned so to be axially in contact with the socket member 1062.

It is to be noted in this respect that the inner diameter of the socket 1062, even in correspondence of ribs 1620 (which protrude radially inwardly) shall be greater than the maximum diameter or anyway transversal dimension of the shaft 2002 in order to allow for an unimpeded sliding over the entire length of the shaft, for reasons which will appear more evident in the following.

Figure 13A:
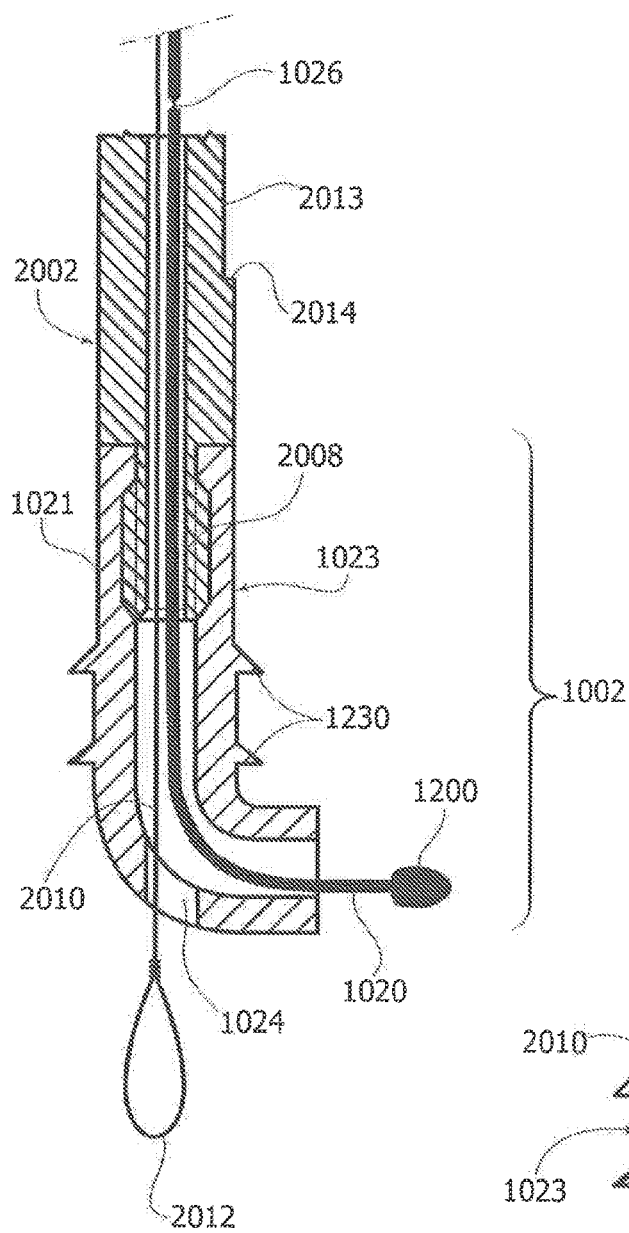

With reference to FIG. 12 (wherein the headings identical to those already used in the previous figures indicate the same objects), the instrument 2000 is introduced into the left atrium via an atrial access point AAP. The proximal end of the instrument is advanced towards the native mitral valve MV. The proximal end is then advanced across the mitral valve between the two native valve leaflets NVL and into the left ventricle LV. Shortly afterwards, it is further displaced radially in a peripheral position with respect to the mitral valve MV. The advancement of the instrument 2000 into the left ventricle is stopped when the end of the plug member 1023 wherefrom the undeployed spire-like member 1020 protrudes reaches a position relative to the chordae tendineae CT which in various embodiments may be substantially halfway between the native valve leaflets NVL and the papillary muscles PM. An enlarged view of the proximal end of the instrument at this stage of the implantation procedure is shown in FIG. 13A.

The spire-like member 1020 is then deployed from the proximal end of the instrument 2000 by acting on the actuator 2020. Thanks to the thermo-forming of the spire-like member 1020, when deployed it immediately recovers a circular pattern, so to enable the practitioner to encircle the chordae tendineae CT by the member 1020 itself. See in this respect the sequence of solid arrows in FIG. 12 located along the member 1020.

In various embodiments, the deployment of the spire-like member 1020 is continued until all the chordae tendineae CT are essentially encircled and until the ogive-like member 1200 meets the loop 2012 of the wire-like member 2010.

Then the practitioner, either by acting on the manipulation assembly (actuators 2020, 2022) or by relying on a separate surgical clamp, may pass the ogive-like member 1200 through the loop 2012. The loop 2012 is configured to intercept the free end of the spire-like member 1020 in the deployed configuration, particularly the ogive-like member 1200.

Figure 13B:
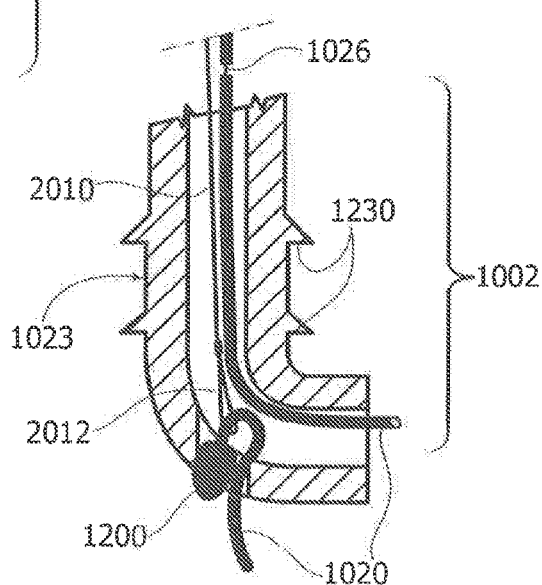

At this stage, the practitioner may pull the wire-like member 2010 by acting on the actuator 2022 and draw the ogive-like member 1200 and a portion of the spire like member 1020 immediately adjacent thereto into the opening 1024. The result of this operation is shown in FIG. 13B.

The opening 1024 and the ogive-like member 1200 shall be sized and dimensioned so that when the latter is drawn into the opening 1024 bent back onto the spire-like member 1020, the total transversal dimension produces a sort of force-fit engagement with the opening 1024 itself. In this way, an essentially closed loop may be created from the spire-like member 1020.

When a firm force-fitting of the free end of the spire like member 1020 (i.e the ogive-like member plus the immediately adjacent portion of the member 1020) into the opening 1024 is attained, the practitioner may exert a further pulling action on the wire-like member 2010, so to cause a failure of the loop which thus breaks open thereby allowing the practitioner to remove the wire-like member 2010 from the instrument 2000.

Additionally, a further pulling action may be exerted on the spire like member 1020 by the actuator 2020 so to cause a failure of the weakened section 1026. The portion of the member 1020 upstream the plug member 1023 can therefore be removed from the instrument 2000. It is to be noted that in various embodiments the weakened section 1026 is positioned so that when the spire like member is fully deployed around the chordae tendineae and force fitted into the opening 1024, it is located just below the end of the threaded portion 1021.

Next, as shown in FIG. 14, the entire instrument 2000 is first raised back up towards the left atrium LA, thereby bringing the closed loop created by the member 1020 into contact with the native valve leaflets NVL (while maintaining the chordae tendineae encircled therein). Note also that following such operation the plug member 1023 is now positioned across the mitral valve, with a portion abutting either the native valve annulus or the native valve leaflets from the ventricle and another portion (i.e. that carrying the circumferential ribs 1230) protruding into the atrium.

Then, the sheath 2015 with the stent member 1006 and the valve 1008 is advanced towards the mitral valve MV: the D-shaped section of the hub 2016 and the shaft 2002 prevents any undesired rotation between the sheath (and the prosthesis held therein) and the shaft, so that no misalignments of the prosthesis may occur.

The socket 1062 attached to the stent member 1006 simply slides down the shaft together with the prosthesis drawn and pushed by the hub 2016.

The final position of the portion 1004, as well as the sheath 2015, is illustrated in FIG. 15. In various embodiments the sheath 2015 is advanced until an engagement is reached of the plug member 1023 and the socket 1062.

In these embodiments the engagement is of the snap-fit type due to the presence of the circumferential ribs 1230 and 1620. Note that the slopes of each circumferential rib on the plug and the socket member are oriented so to allow a relative movement between the former and the latter only in the direction of engagement thereof, thereby preventing any undesired disengagement in a way at least roughly similar to a ratchet and pawl mechanism.

The socket member 1062 can be driven into engagement with the plug member by acting on the sheath 2015, i.e. by displacing the latter in a proximal direction towards the plug member 1023: the same action will be imparted to the hub 2016 and transferred to the socket member 1062 thanks to the contact therebetween.

Also note that, while the socket member 1062 is capable of sliding past the abutment shoulder 2014, the hub is impeded for the reasons explained in the foregoing. The abutment shoulder therefore acts as an axial stop member, preventing the sheath 2015 from travelling too far down the shaft 2002, thereby avoiding damages to the prosthesis, the surrounding tissues and the patient. Moreover, in various embodiments it is preferable to axially dimension the flat side surface 2013, the socket member 1062 and the hub 2016 so to leave an axial gap (although a small one) between the latter and the abutment surface 2014 even after complete engagement of the socket 1062 onto the plug 1023. This in order to prevent the sheath 2015 from coming to a halt before a complete engagement between the socket 1062 and the plug 1023 is reached and in order to have a further safety margin for the axial travel of the sheath 2015 along the shaft 2002.

Figure 16:
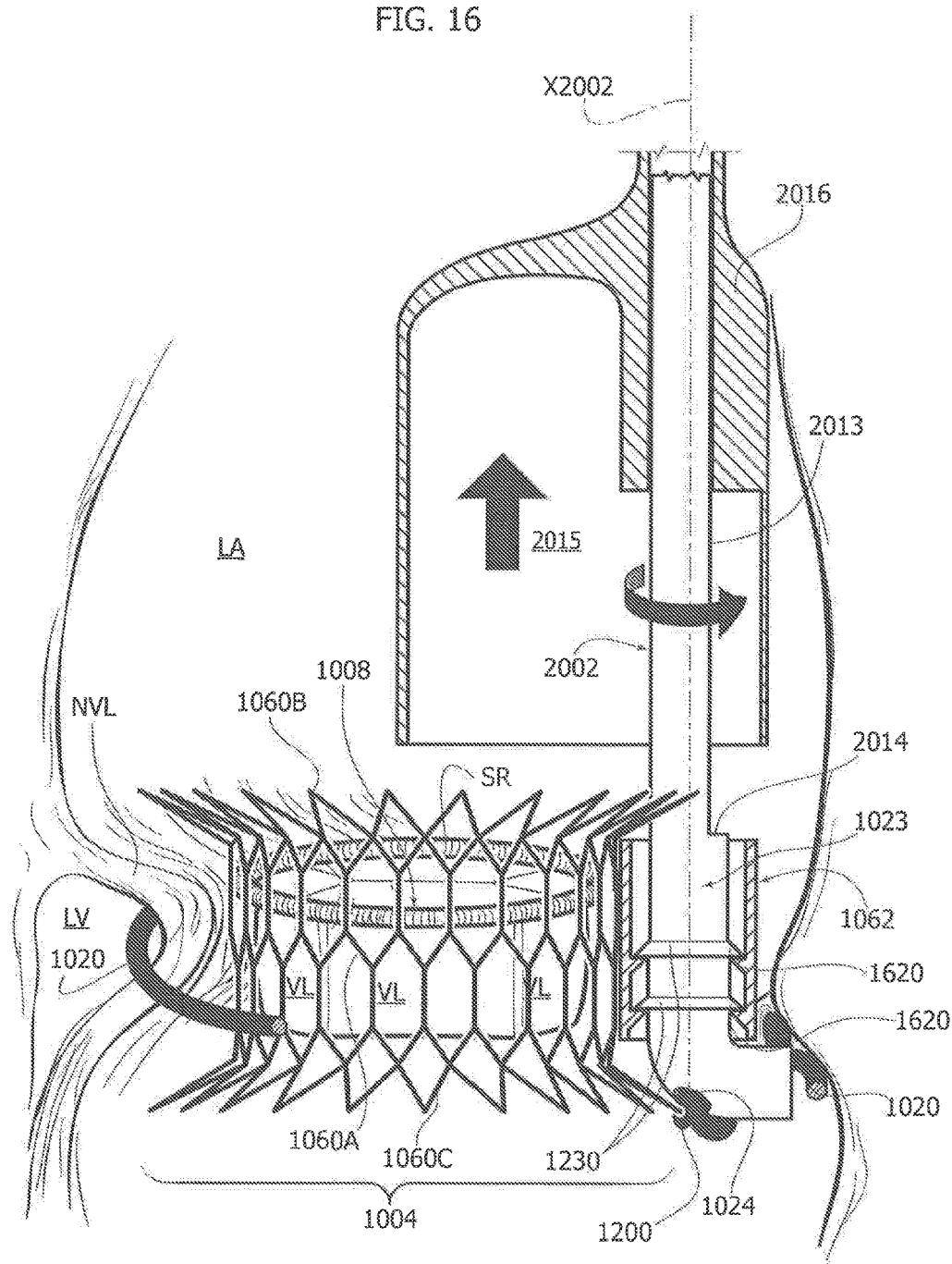

With reference to FIG. 16, once the engagement between the plug and the socket member is reached, the sheath may be retracted distally away from the implantation site so to allow a radial expansion of the stent member 1006. In some embodiments, the expansion capabilities of the stent member 1006 may be such that no post-expansion is needed. In other embodiments, the expansion capabilities may be chosen so that a post expansion through a balloon (not shown) may be necessary.

In various embodiments, upon expansion of the stent member 1006 the mesh portions 1060B and 1060C regain a flared pattern so to further enhance the anchoring of the prosthesis above and below the valve annulus.

After retracting the sheath 2015, in various embodiments the practitioner may separate the instrument 2000 from the proximal portion thereof, i.e. from the plug member 1023, simply by unscrewing the shaft 2002 from the plug member 1023. Equivalently, in embodiments wherein other connections than a threaded one are envisaged, the practitioner may act upon the connection so as to release the coupling.

The plug member 1023 therefore remains at the implantation site as part of the prosthesis 1000.

The result is, similarly to the prosthesis 1, that of an implanted heart valve prosthesis wherein the first portion 1002 is implanted in the ventricle, while the first portion, coupled to the first portion by means of the snap-fit engagement between the socket and the plug members, is implanted at the cardiac valve annulus.

The man skilled in the art may thus readily appreciate how rapidly the implantation of the prosthesis 1000 may be performed. The instrument 2000 is at the same time operable to deliver and deploy the prosthesis at the implantation site and configured so to provide also a portion of the prosthesis 1000 itself (i.e. the plug member 1023).

There is no need for complex positioning operations of the portion 1004 carrying the prosthetic valve 1008, it already comes properly oriented and ready for the snap fit engagement with the plug member, which occurs simply by sliding the prosthesis along the shaft of the instrument 2000.

Figure 17:
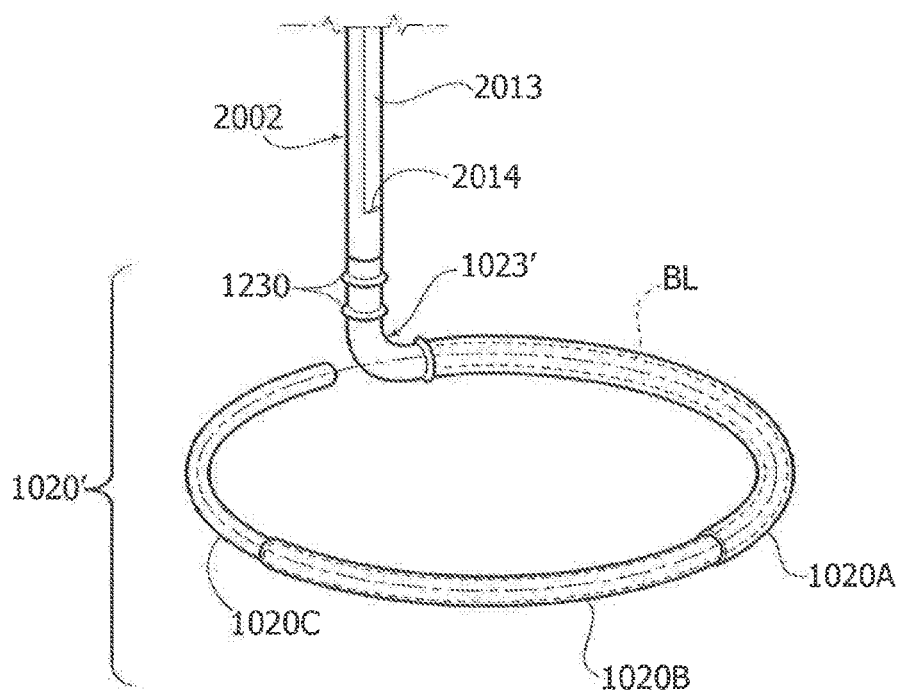
FIGS. 17 and 18 are a perspective and a sectional view of a component according to a further embodiment of the prosthesis of FIG. 10.
Figure 18:
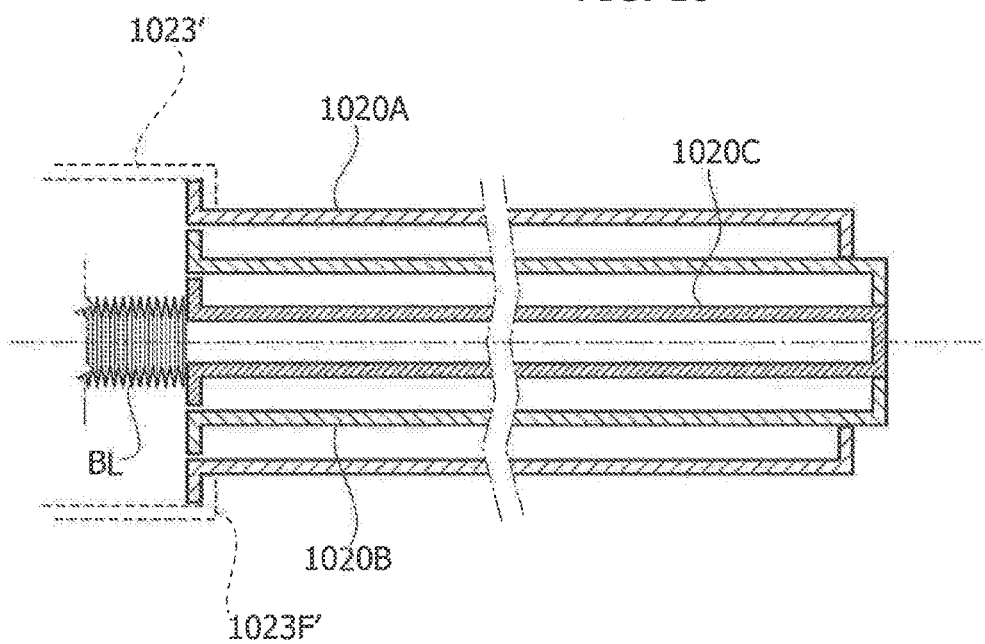

With reference now to FIGS. 17-18, a variant of both the prosthesis 1000 and the instrument 2000 is therein depicted. The headings identical to those already adopted in the foregoing denote the same components.

According to such variant, a first portion 1002 of the prosthesis includes a telescopic spire-like member 1020' including, in the embodiment specifically illustrated herein, three telescoped segments 1020A, 1020B, 1020C. As visible in FIG. 18, in an undeployed condition the telescoped segment 1020A already protrudes with respect to the plug member 1023 and is in abutment against an annular flange 1023F' of the plug member 1023.

An inflatable balloon BL is housed deflated and axially compressed inside the shaft 2002 and the plug member 1023, and it is fixed at one end to the segment 1020C, which is the smallest in diameter.

After introducing the instrument 2000 across the implantation site as shown in FIG. 12, the telescopic spire-like member 1020' is deployed by inflating the balloon BL, for example by relying upon the lumen provided inside the shaft 2002 and the plug member 1023 (both hollow, the latter with no opening 1024). In this variant there is thus no need for deploying a spire-like member and intercepting the latter with a loop as in other embodiments herein presented, thereby further simplifying the implantation of the prosthesis.

The remainder of the implantation sequence is essentially unchanged.

Of course, although in the foregoing disclosure a number of formal expressions such as "in one embodiment", "in some embodiments", "in other embodiments", "in various embodiments", and "in further embodiments", have been used, it is to be understood that the present disclosure is intended to cover also embodiments resulting from the combination of features described in relation to embodiments which are introduced separately by such formal expressions, of course where such features are not evidently incompatible with each other.

Additionally, preferred embodiments of the invention include, for example:

Embodiment 1. a heart valve prosthesis configured to be implanted at cardiac valve annulus located at an interface between a ventricle and an atrium, the heart valve prosthesis including:

a first portion configured for enclosing a plurality of chordae tendineae in the ventricle and native valve leaflets to which said chordae tendineae are connected, and a second portion including a radially expandable annular member and a prosthetic heart valve anchored to said radially expandable annular member, wherein said first portion is configured to be implanted in the ventricle, and wherein said second portion is configured to be implanted and coupled to the first portion at the cardiac valve annulus.

Embodiment 2: the heart valve prosthesis according to Embodiment 1, wherein the second portion is configured to be coupled to the first portion in a snap-fit fashion.

Embodiment 3: the heart valve prosthesis of Embodiment 2, wherein the first portion includes a spire-like member having a plug member configured to be coupled to a socket on the second portion.

Embodiment 4: the heart valve prosthesis according to any of the previous Embodiments, wherein the radially expandable annular member of the second portion is a stent member.

Embodiment 5: the heart valve prosthesis according to Embodiment 4, wherein said stent member includes a first mesh portion and a second and a third mesh portions at opposite ends of said first mesh portion, wherein said first mesh portion has a generally cylindrical shape and said second and third mesh portions have a flared pattern.

Embodiment 6: the heart valve prosthesis of Embodiment 5, wherein said socket member is fixed to said first mesh portion.

Embodiment 7: the heart valve prosthesis according to any of Embodiments 3 to 6, further including an instrument for the implantation thereof including:
a proximal tip;
a shaft,
a sheath slidably mounted along said shaft and configured for holding the stent member of said second portion in a radially collapsed state,
a manipulation assembly,
wherein said plug member defines said proximal tip,
wherein said shaft is releasably coupled to said plug member, and
wherein said second portion is mounted inside said sheath so that said socket member is also slidably mounted onto said shaft.

Embodiment 8: the heart valve prosthesis of Embodiment 7, wherein said shaft includes a portion with a D-shaped cross section and having a flattened side surface, wherein said flattened side surface terminates at an abutment shoulder
wherein said sheath includes a hub by which the slidable coupling with the shaft is attained and having a D-shaped cavity matching the D-shaped cross section of said portion of the shaft.

Embodiment 9: the heart valve prosthesis of Embodiment 8, wherein said hub abuts on said socket member when stent member of the second portion is held within the sheath.

Embodiment 10: the heart valve prosthesis of Embodiment 9, wherein the socket member configured to be driven into engagement with the plug member by displacement of the sheath in a proximal direction along the shaft during implantation.

Embodiment 11: the heart valve prosthesis according to any of Embodiments 7 to 10, wherein the spire-like member includes a deployable thermo-formed wire housed within the shaft and the plug member in a linear configuration and protruding from the plug member at one end thereof, wherein the instrument further includes a wire-like member also housed within the shaft and coming out of said plug member, said wire-like member terminating in a loop configured to intercept a free end of the spire like member in a deployed configuration thereof.

Embodiment 12: the heart valve prosthesis of Embodiment 11, wherein said spire-like member includes an ogive-like member at said free end, wherein said loop is configured to intercept said ogive-like member so that said free end of the spire-like member, including said ogive-like member, may be drawn into force-fit engagement into an opening in said plug member wherefrom said wire-like member comes out by pulling said wire-like member.

Embodiment 13: the heart valve prosthesis of any of Embodiments 5 to 12, wherein said first portion includes a telescopic spire-like member consisting of a plurality of telescoped segments configured to be deployed by means of an inflatable balloon held deflated and axially compressed within said shaft and said plug member.

Embodiment 14: the heart valve prosthesis according to Embodiment 4, wherein said stent member includes a first mesh portion and a second mesh portion, wherein said first mesh portion and said second mesh portion both extend in a circumferential direction and wherein said first mesh portion further extends in a radial direction while said second mesh portion extends in an axial direction, wherein said socket member is coupled to said first mesh portion.

Embodiment 15: the heart valve prosthesis according to any of Embodiments 3 to 4 and 13 to 14, wherein the spire-like member has a circumferential development with a first and a second free ends, wherein said plug member is located near one of said free ends.

The invention claimed is:

1. A heart valve prosthesis configured to be implanted at a cardiac valve annulus located at an interface between a ventricle and an atrium, the heart valve prosthesis including:
a first portion configured for enclosing a plurality of chordae tendineae in the ventricle and native valve leaflets to which said chordae tendineae are connected, and
a second portion including a radially expandable annular member and a prosthetic heart valve anchored to said radially expandable annular member,
wherein said first portion is configured to be implanted in the ventricle, and said second portion is configured to be implanted and coupled to the first portion at the cardiac valve annulus, and
wherein the radially expandable annular member of the second portion includes a mesh stent member and the first portion includes a spire-like member having a plug member configured to be coupled to a socket member attached to the mesh stent member of the second portion.

2. The heart valve prosthesis of claim 1, wherein the second portion is configured to be coupled to the first portion in a snap-fit fashion.

3. The heart valve prosthesis of claim 1, wherein said mesh stent member includes a first mesh portion and a-second and a-third mesh portions at opposite ends of said first mesh portion, wherein said first mesh portion has a generally cylindrical shape and said second and third mesh portions have a flared pattern.

4. The heart valve prosthesis of claim 3, wherein said socket member is fixed to said first mesh portion.

5. The heart valve prosthesis of claim 1, further including an instrument for the implantation thereof including:
a proximal tip;
a shaft,
a sheath slidably mounted along said shaft and configured for holding the mesh stent member of said second portion in a radially collapsed state,
a manipulation assembly,
wherein said plug member defines said proximal tip,
wherein said shaft is releasably coupled to said plug member, and
wherein said second portion is mounted inside said sheath so that said socket member is also slidably mounted onto said shaft.

6. The heart valve prosthesis of claim 5, wherein said shaft includes a portion with a D-shaped cross section and having a flattened side surface, wherein said flattened side surface terminates at an abutment shoulder wherein said sheath includes a hub by which the slidable coupling with the shaft is attained and having a D-shaped cavity matching the D-shaped cross section of said portion of the shaft.

7. The heart valve prosthesis of claim 6, wherein said hub abuts on said socket member when said mesh stent member of the second portion is held within the sheath.

8. The heart valve prosthesis of claim 7, wherein the socket member configured to be driven into engagement with the plug member by displacement of the sheath in a proximal direction along the shaft during implantation.

9. The heart valve prosthesis of claim 5, wherein the spire-like member includes a deployable thermo-formed wire housed within the shaft and the plug member in a linear configuration and protruding from the plug member at one end thereof, wherein the instrument further includes a wire-like member also housed within the shaft and coming out of said plug member, said wire-like member terminating in a loop configured to intercept a free end of the spire like member in a deployed configuration thereof.

10. The heart valve prosthesis of claim 9, wherein said spire-like member includes an ogive-like member at said free end, wherein said loop is configured to intercept said ogive-like member so that said free end of the spire-like member, including said ogive-like member, may be drawn into force-fit engagement into an opening in said plug member wherefrom said wire-like member comes out by pulling said wire-like member.

11. The heart valve prosthesis of claim 5, wherein said first portion includes a telescopic spire-like member consisting of a plurality of telescoped segments configured to be deployed by means of an inflatable balloon (BL) held deflated and axially compressed within said shaft and said plug member.

12. The heart valve prosthesis of claim 1, wherein said mesh stent member includes a first mesh portion and a second mesh portion, wherein said first mesh portion and said second mesh portion both extend in a circumferential direction and wherein said first mesh portion further extends in a radial direction while said second mesh portion extends in an axial direction, wherein said socket member is coupled to said first mesh portion.

13. The heart valve prosthesis of claim 1, wherein the spire-like member has a circumferential development with first and second free ends, wherein said plug member is located near one of said first and second free ends.

* * * * *